(12) United States Patent
Portnoy et al.

(10) Patent No.: US 7,749,510 B2
(45) Date of Patent: Jul. 6, 2010

(54) METHODS OF ELICITING OR BOOSTING A CELLULAR IMMUNE RESPONSE

(75) Inventors: Daniel A. Portnoy, Albany, CA (US); Richard Lane Calendar, Berkeley, CA (US); Peter M. Lauer, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 440 days.

(21) Appl. No.: 10/547,999

(22) PCT Filed: Apr. 29, 2003

(86) PCT No.: PCT/US03/13492

§ 371 (c)(1),
(2), (4) Date: Sep. 7, 2006

(87) PCT Pub. No.: WO03/092600

PCT Pub. Date: Nov. 13, 2003

(65) Prior Publication Data

US 2007/0059322 A1  Mar. 15, 2007

Related U.S. Application Data

(63) Continuation-in-part of application No. 10/136,860, filed on Apr. 30, 2002, now Pat. No. 7,425,449.

(51) Int. Cl.
*A61K 39/02* (2006.01)
(52) U.S. Cl. .................. 424/234.1; 424/200.1; 424/93.2
(58) Field of Classification Search ........................ None
See application file for complete search history.

(56) References Cited

U.S. PATENT DOCUMENTS 5,830,702 A    11/1998  Portnoy et al.
6,099,848 A *   8/2000  Frankel et al. ........... 424/246.1

FOREIGN PATENT DOCUMENTS

| WO |       99/07861 | * | 2/1999 |
| WO | WO 99/07861 |   | 2/1999 |
| WO | WO 99/25376 |   | 5/1999 |
| WO | WO 00/09733 |   | 2/2000 |
| WO | WO 02/08431 |   | 1/2002 |

OTHER PUBLICATIONS

Loessner et al, Molecular Microbiology, 35(2):324-340, 2000.*
Smith et al eds Methods in Microbiology, vol. 29, Genetic Methods for Divers Prokaryotes, Academic Press Inc. 1999, pp. 117-118.*
Yang et al (Journal of Bacteriology, 184(7):1859-1864, 2002).*
Rossingol et al (FEMS Microbiology Letters, 213:45-49, 2002).*
Moreau et al, (Microbiology 145:539-548, 1999).*
Luong et al, (Journal of Microbiological Methods 70:186-189, 2007 ).*
McShan et al (Methods in Cell Science 20:51-57, 1998).*
Lillehaug et al (Gene 188:129-136, 1997).*
Lee et al Gene 103:101, 1991 abstract only.*
Lauer et al "Construction, Characterization, and Use of Two Listerla Monocytogenes Site-Specific Phage Intergration Vectors" Journal of Bacteriology, Aug. 2002, vol. 184. No. 15, pp. 4177-4186.
Schaferkodt et al. "Vector Plasmid for Insertional Mutagenesis and Directional Cloning in Listeria spp" BioTechniques, 1995 vol. 19 No. 5, pp. 720-725.
Fortineau et al "Optimization of Green Fluorescent Protein Expression Vectors for InVitro and In Vivo Detection of Listeria Monocytogenes" Res. Microbiol. 2000, vol. 151. pp. 353-360.
Reiter et al. "Transfer RNA Genes Frequently Serve As Integration Sites For Prokaryotic Genetic Elements" Nucleic Acids Research, 1989, vol. 17, No. 5. pp. 1907-1914.
Scott et al. "Conjugative Transposition" Annu. Rev, Microblol. 1995, vol. 49, pp. 367-397.
Shen et al. "Recombinant Listeria monocytogenes as a live vaccine vehicle for the induction of protective anti-viral cell-mediated immunity." Proc. Nat'l Acad. Sci. ,USA, Apr. 1995, vol. 92, No. 9, pp. 3987-3991.
Loessner et al. (Molecular Microbiology, 35(2):324-340, 2000), Mar. 28, 2008.
Hodgson et al. (Molecular Microbiology, 35(2):312-323, 2000).
Autret, et al. "Identification of New Genes Involved in the Virulence of Listeria monocytogenes by Signature-Tagged Transposon Mutagenesis," (2001) 69(4):2054-2065.
Autret N. et al "Identification of New Genes Involved in the Virulence of *Listeria monocytogenes* by Signature-Tagged Transposon Mutagenesis" Infection and Immunity (Apr. 2001) 69(4):2054-2065.
Fortineau N. et al "Optimization of green fluorescent protein expression vectors for in vitro and in vivo detection of *Listeria monocytogenes*" Res Microbiol (2000) 151:353-360.
Schaferkordt S et al "Vector Plasmid for Insertional Mutagenesis and Directional Cloning in *Listeria* spp " Bio Techniques (Nov. 1995) 19:720-725.
Shen H et al "Recombinant *Listeria monocytogenes* as a live vaccine vehicle for the induction of protective anti-viral cell-mediated immunity" Proc Natl Acad Sci USA (Apr. 1995) 92:3987-3991.

* cited by examiner

*Primary Examiner*—Patricia A Duffy
(74) *Attorney, Agent, or Firm*—Bret E. Field; Bozicevic, Field & Francis LLP

(57) ABSTRACT

Site-specific Listeria integration vectors and methods for their use are provided. The subject vectors include a bacteriophage integrase gene and a bacteriophage attachment site, where in many embodiments the bacteriophage that is the source of these elements is a listeriophage. In certain embodiments, the subject vectors further include a multiple cloning site, where the multiple cloning site may further include a polypeptide coding sequence, e.g., for a heterologous antigen. The subject vectors and methods find use in a variety of different applications, including the study of Listeria species and the preparation of Listeria vaccines.

10 Claims, 4 Drawing Sheets

A.

B.

```
352   AGTGCCATTTTGTCCTGATAGCTCAGCTGGATAGAGCAACGGCCTTCTAAGCCGTCGGTCGGGGGTTCGAATCCCTCTCAGGACGTAAATAGCTAT
         :        ::    : :  ::      :       :    :     :  : ::  ::::::::::::::::  ::      ::
19228 TTACATAAAATGTTTGTGGTATTATTTGTGGTATATATATCCTAAATGGCTTTATATCAGTGTCTGTTAATCCCTCTCAGGACGTTAAATAGTAA
```

METHODS OF ELICITING OR BOOSTING A CELLULAR IMMUNE RESPONSE

CROSS-REFERENCE TO RELATED APPLICATIONS

This application is a continuation-in-part of application Ser. No. 10/136,860 filed Apr. 30, 2002; the disclosure of which is herein incorporated by reference.

ACKNOWLEDGMENT OF GOVERNMENT SUPPORT

This invention was made with Government support under Grant Nos. 1 R37 AI29619 and 1 R01 AI27655 awarded by the National Institute of Health. The Government has certain rights in this invention.

INTRODUCTION

1. Field of the Invention

The field of this invention is *Listeria* species, e.g., *Listeria monocytogenes*, particularly recombinant strains of *Listeria* species, and methods for their fabrication and use.

2. Background of the Invention

*Listeria monocytogenes* is a Gram-positive, food-borne human and animal pathogen responsible for serious infections in immunocompromised individuals and pregnant women. Severe *L. monocytogenes* infections in humans are characterized by meningitis, meningoencephalitis, septicemia, and fetal death. *L. monocytogenes* is ubiquitous in nature and, in addition, can be isolated from a wide variety of warm blooded animals.

Protocols for recombinantly engineering *Listeria* species are of interest in both research and therapeutic applications. For example, *Listeria* species transformation protocols find use in the elucidation of the mechanisms responsible for growth and virulence of these types of bacteria. In addition, such protocols also find use in the preparation of live *Listeria* vaccines, which vaccines find use in a variety of different medical applications.

To date, a variety of different protocols have been employed to transform *Listeria* species, where such protocols include: homologous recombination, transposon based recombination, etc. While different protocols are currently available for engineering *Listeria* species, such methods are not entirely satisfactory. Disadvantages currently experienced with one or more of the available protocols include: (1) instability of the expression cassette in the transformed species; (2) variable impact on virulence of the transformed species; (3) size constraints of the expression cassette that can be placed in the transformed species; etc.

As such, despite the variety of different transformation protocols available, there is continued interest in the identification of further transformation protocols that can expand the repertoire of available genetic tools. Of particular interest would be the development of an efficient, site-specific integration vector that was suitable for use with a wide array of different *Listeria* species, where the vector did not suffer from one or more of the above disadvantages of the currently available protocols.

Relevant Literature

Patents and published patent applications of interest include: U.S. Pat. No. 5,830,702 and published PCT application serial nos.: WO 99/25376 and WO 00/09733.

SUMMARY OF THE INVENTION

Site-specific *Listeria* species integration vectors and methods for their use are provided. The subject vectors include a bacteriophage integrase gene and a bacteriophage attachment site, where in many embodiments the bacteriophage that is source of these elements is a listeriophage. In certain embodiments, the subject vectors further include a multiple cloning site, where the multiple cloning site may further include a coding sequence, e.g., a coding sequence for a heterologous polypeptide, etc. The subject vectors and methods find use in a variety of different applications, including the study of *Listeria* species and the preparation of *Listeria* species. vaccines.

DESCRIPTION OF THE SPECIFIC EMBODIMENTS

Figure 1:
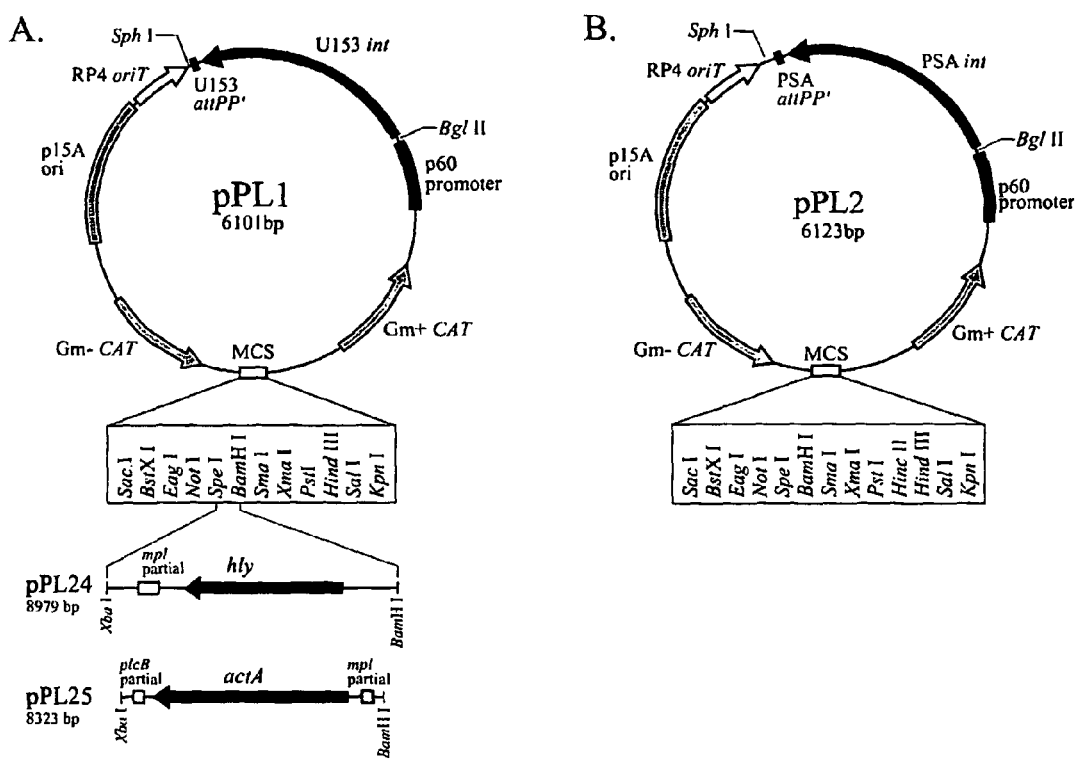
FIG. 1. (A) Plasmid map of the pPL1 integration vector. SEQ ID NO:24 provides the sequence of pPL1. Chloramphenicol resistance genes and *E. coli* origin of replication are shown in grey, RP4 origin of transfer shown in white, integrase gene and *L. monocytogenes* p60 promoter shown in black. Multiple cloning site is shown at the bottom of the plasmid with unique restriction sites noted below the MCS in a box. pPL24 and pPL25 inserts are shown schematically below the MCS and were cloned as described in Materials and Methods. Final sizes of the plasmid constructs and the restriction sites used in cloning are noted with each of the inserts. (B) Plasmid map of the integration vector pPL2. SEQ ID NO:28 provides the sequence of pPL2. The color scheme and genes are the same as in FIG. 1A except the PSA integrase and PSAattPP' sites as noted. The multiple cloning site with 13 unique restriction sites is shown at the bottom of the plasmid.
Figure 2:
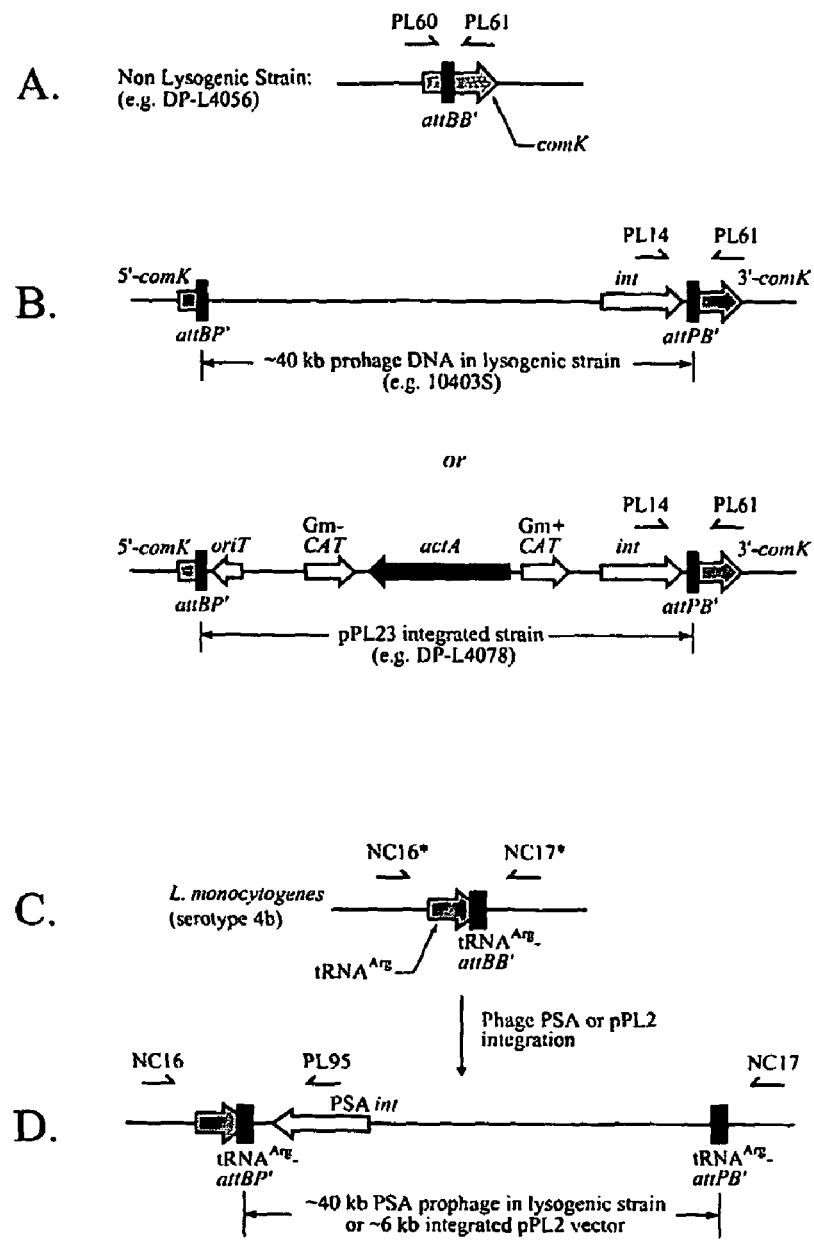
FIG. 2. Genomic organization of the attachment sites within the comK gene (A and B) and the tRNA$^{Arg}$ gene (C and D). (A) Non-lysogenic *L. monocytogenes* strain, with an intact comK gene. Primers PL60 and PL61 amplify across the bacterial attachment site comK-attBB'. (B) Lysogenic *L. monocytogenes* strain (with approximately 40 kb of phage DNA inserted into the comK gene) or integrated strain (with pPL1 construct inserted into the comK gene). Primers PL14 and PL61 amplify across the hybrid attachment site comK-attPB'. (C) *L. monocytogenes* serotype 4b strain non-lysogenic at tRNA$^{Arg}$-attBB'. Primers NC16 and NC17 amplify across the bacterial attachment site tRNA$^{Arg}$-attBB' in serotype 4b strains. Asterisk indicates primers NC16 and NC17 are substituted with PL102 and PL103 to amplify across the bacterial attachment site tRNA$^{Arg}$-attBB' in serotype 1/2 strains. (D) Lysogenic *L. monocytogenes* strain (with approximately 40 kb of phage DNA or 6 kb pPL2 vector DNA inserted at the 3' end of the tRNA$^{Arg}$ gene. Primers NC16 and PL95 amplify across the hybrid attachment site tRNA$^{Arg}$-attBP' in both serotype 4b and 1/2 strains.

Site-specific *Listeria* species integration vectors and methods for their use are provided. The subject vectors include a bacteriophage integrase gene and a bacteriophage attachment site, where in many embodiments the bacteriophage that is source of these elements is a listeriophage. In certain embodiments, the subject vectors further include a multiple cloning site, where the multiple cloning site may further include a coding sequence, e.g., for a heterologous polypeptide, etc. The subject vectors and methods find use in a variety of different applications, including the study of *Listeria* species and the preparation of *Listeria* species vaccines.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices and materials are now described.

All publications mentioned herein are incorporated herein by reference for the purpose of describing various invention components that are described in the publications which might be used in connection with the presently described invention.

In further describing the subject invention, the subject vectors are reviewed first in greater detail, followed by a review of the methods of using the subject vectors, as well as representative applications in which the subject vectors and methods find use.

Vectors

As summarized above, the subject invention provides *Listeria* site-specific integration vectors, i.e., vectors that integrate into *Listeria* genomes in a site-specific manner. The subject vectors are characterized in that they stably integrate into a genome of a *Listeria* species in a site-specific, as opposed to random, manner. As the subject vectors integrate site-specifically into a target genome, the vectors of the subject invention typically are inserted into a specific location or sequence (i.e., domain, location) of the target genome by a mechanims mediated by a recombinase, specifically an integrase, where the integrase is one that uses two distinct recognition sites as substrates, one of which is positioned in the integration site of the target genome (the site into which a nucleic acid is to be integrated) and another adjacent a nucleic acid of interest to be introduced into the integration site (i.e., a site on the subject vector referred to herein as the "bacteriophage attachment site"). For example, the recognition sites for phage integrases are generically referred to as attB, which is present in the bacterial genome (into which nucleic acid is to be inserted) and attP (which is present in the phage nucleic acid adjacent the nucleic acid for insertion into the bacterial genome, which is referred to herein as the "bacteriophage attachment site"). Recognition sites can be native (endogenous to a target genome) or altered relative to a native sequence. Use of the term "recognize" in the context of an integrase "recognizes" a recognition sequence, is meant to refer to the ability of the integrase to interact with the recognition site and facilitate site-specific recombination.

The subject vectors are capable of integrating into the genomes of a wide variety of different *Listeria* species. Integration is readily determined by using any convenient assay, including those known to those of skill in the art, that can identify whether or not vector DNA has integrated into the genomic DNA of a target organism. For example, vector DNA can be introduced into a target organism, e.g., via conjugation, and then integration can be determined via PCR amplification of the integrated sequence using primers flanking the target site, where the size of the amplification product is determinative of whether integration has occurred. An example of such an assay is provided in the experimental section, below. Additional features of many embodiments of the subject vectors is that they replicate autonomously in a non-*Listeria* host cell, e.g., *E. coli*, and are stable and innocuous in such non-*Listeria* host cells.

The subject integration vectors are typically double-stranded plasmid vectors, where the vectors are generally at least about 3 kb, often at least about 5 kb and may be large as 15 kb, 20 kb, 25 kb, 30 kb or larger, where the vectors sometimes range in size from about 3-6 to about 20 kb. The vectors include a number of structural features that impart to the vectors the above-described functional characteristics.

One structural feature of the subject vectors is a bacteriophage integrase gene, i.e., a nucleic acid coding sequence for a bacteriophage integrase, which is operably linked to a *Listeria* specific promoter, such that the gene (coding sequence) is expressed in the *Listeria* cell for which the vector is designed to be employed. In many embodiments, the bacteriophage integrase gene is one obtained from a listeriophage, i.e., it is a listeriophage integrase gene. A variety of different listeriophages are known in the art, where any convenient listeriophage may serve as the source of the integrase gene, i.e., the integrase encoding nucleic acid. Specific integrases of interest include, but are not limited to: the U153 integrase, the PSA integrase; and the like.

As indicated above, the integrase gene is operably linked to a promoter (as well as regulatory and/or signal sequences, if necessary) that drives expression of the integrase gene when the vector is present in the *Listeria* cell for which the vector is designed and in which integration of the vector is desired. Any convenient promoter may be employed, where in certain embodiments the promoter is a *Listeria* specific promoter. Representative promoters of interest include, but are not limited to: the *Listeria* p60 promoter, the *Listeria* actA promoter, the *Listeria* plcA promoter, the *Listeria* mpl promoter, the *Listeria* plcB promoter, the *Listeria* inlA promoter; a heat shock promoter; and the like Promoters may also include certain bacteriophage promoters such as the promoters for T7, Qβ, SP6 and the like if the strain of *Listeria* also expresses the cognate bacteriophage RNA polymerase. In addition to the integrase gene/promoter element described above, the subject vectors also include a phage attachment site, i.e., a sequence or domain of nucleotides that provide for a site-specific integration with a *Listeria* genome. Any convenient phage attachment site may be employed, where selection of the phage attachment site will depend, at least in part, on the desired integration location for the vector. Representative phage attachment sites of interest include, but are not limited to: the comK integration site (as described in greater detail in the experimental section below); the tRNA$^{Arg}$ integration site (as described in greater detail in the experimental section below); and the like.

In addition, the subject vectors may include an origin of replication that provides for replication of the vector in a non-*Listeria* host cell, e.g., *E. coli*. This origin of replication may be any convenient origin of replication or ori site, where a number of ori sites are known in the art, where particular sites of interest include, but are not limited to: p15A; pSC101; ColEI; pUC; pMB9; and the like.

In addition, the subject vectors may include an origin of transfer site or element when convenient, e.g., when the vector is introduced in the target *Listeria* cell using a conjugation protocol, as described in greater detail below. Any convenient origin of transfer (oriT) may be employed, where representative origins of transfer of interest include, but are not limited to: RP4 oriT; RSF1010 oriT; and the like.

In addition, the subject vectors typically include at least one restriction endonuclease recognized site, i.e., restriction site, which is located on the vector at a location which is amenable to insertion of a heterologous gene/expression cassette. A variety of restriction sites are known in the art and may be present on the vector, where such sites include those recognized by the following restriction enzymes: HindIII, PstI, SalI, AccI, HincII, XbaI, BamHI, SmaI, XmaI, KpnI, SacI, EcoRI, BstXI, EagI, NotI, SpeI and the like. In many embodiments, the vector includes a polylinker or multiple cloning site, i.e., a closely arranged series or array of sites recognized by a plurality of different restriction enzymes, such as those listed above.

In certain embodiments, the subject vectors include at least one coding sequence, e.g., a coding sequence for heterologous polypeptide/protein coding sequence present in the multiple cloning site, e.g., as a result of using a restriction endonuclease site present in the multiple cloning site to insert the coding sequence into the vector, according to well known recombinant technology protocols. By "heterologous" is meant that the coding sequence encodes a product, e.g., a protein, peptide, polypeptide, glycoprotein, lipoprotein, or other macromolecule, that is not normally expressed in *Listeria*. In many embodiments, this coding sequence is part of an expression cassette, which provides for expression of the coding sequence in the *Listeria* cell for which the vector is designed. The term "expression cassette" as used herein refers to an expression module or expression construct made up of a recombinant DNA molecule containing at least one desired coding sequence and appropriate nucleic acid sequences necessary for the expression of the operably linked coding sequence in a particular host organism, i.e., the *Listeria* cell for which the vector is designed, such as the promoter/regulatory/signal sequences identified above, where the expression cassette may include coding sequences for two or more different polypeptides, or multiple copies of the same coding sequence, as desired. The size of the coding sequence and/or expression cassette that includes the same may vary, but typically falls within the range of about 25-30 to about 6000 bp, usually from about 50 to about 2000 bp. As such, the size of the encoded product may vary greatly, and a broad spectrum of different products may be encoded by the expression cassettes present in the vectors of this embodiment.

The nature of the coding sequence and other elements of the expression cassette may vary, depending on the particular application of the vector, e.g., to study *Listeria* species, to produce *Listeria* species vaccines, for cytosolic delivery of macromolecules, etc. For example, where the vectors are employed in the production of *Listeria* vaccines, the coding sequence may encode a heterologous antigen, where representative heterologous antigens of interest include, but are not limited to: (a) viral antigens, e.g., influenza np protein, HIV gag protein, HIV env protein or parts thereof, e.g., gp120 and gp41, HIV nef protein, HIV pol proteins, HIV reverse transcriptase, HIV protease, herpes virus proteins, etc., (b) malarial antigens; (c) fungal antigens; (d) bacterial antigens; (e) tumor and tumor related antigens; and the like. Due to the flexibility of the vector system, virtually any coding sequence of interest may be inserted. Where secretion of the product encoded by the expression cassette is desired, the expression cassette may include a coding sequence for a fusion protein of a selected foreign antigen and a protein that directs secretion, e.g., Listeriolysin O or PI-PLC; a signal sequence, such as hemolysin signal sequence, etc. Where the subject vectors are employed in the preparation of *Listeria* delivery vehicles, e.g., as described in PCT publication no. WO 00/09733 (the priority application of which is herein incorporated by reference); and Dietrich et al., Nature Biotechnology (1998) 16: 181-185, the heterologous polypeptide coding sequence may be a cytolysin, e.g., phospholipase, pore forming toxin, listeriolysin O, streptolysin O, perfringolysin O, acid activated cytolysins, phage lysins, etc. Other coding sequences of interest include, but are not limited to: cytokines, costimulatory molecules, and the like. As indicated above, the vector may include at least one coding sequence, where in certain embodiments the vectors include two or more coding sequences, where the coding sequences may encode products that act concurrently to provide a desired results.

In general, the coding sequence may encode any of a number of different products and may be of a variety of different sizes, where the above discussion merely provides representative coding sequences of interest.

Methods of Preparing the Subject Vectors

The vectors of the subject invention may be produced using any convenient protocol, including by standard methods of restriction enzyme cleavage, ligation and molecular cloning. One protocol for constructing the subject vectors includes the following steps. First, purified nucleic acid fragments containing desired component nucleotide sequences as well as extraneous sequences are cleaved with restriction endonucleases from initial sources. Fragments containing the desired nucleotide sequences are then separated from unwanted fragments of different size using conventional separation methods, e.g., by agarose gel electrophoresis. The desired fragments are excised from the gel and ligated together in the appropriate configuration so that a circular nucleic acid or plasmid containing the desired sequences, e.g. sequences corresponding to the various elements of the subject vectors, as described above is produced. Where desired, the circular molecules so constructed are then amplified in a host, e.g. *E. coli*. The procedures of cleavage, plasmid construction, cell transformation and plasmid production involved in these steps are well known to one skilled in the art and the enzymes required for restriction and ligation are available commercially. (See, for example, R. Wu, Ed., Methods in Enzymology, Vol. 68, Academic Press, N.Y. (1979); T. Maniatis, E. F. Fritsch and J. Sambrook, Molecular Cloning: A Laboratory Manual, Cold Spring Harbor Laboratory Press, Cold Spring Harbor, N.Y. (1982); Catalog 1982-83, New England Biolabs, Inc.; Catalog 1982-83, Bethesda Research Laboratories, Inc. An example of how to construct a vector of the present invention is provided in the Experimental section, below.

Methods

Also provided by the subject invention are methods of using the above described *Listeria* site specific integration vectors to integrate a heterologous nucleic acid into a *Listeria* genome. In practicing the subject methods, a vector of the subject invention is introduced into a target *Listeria* cell under conditions sufficient for integration of the vector into the target cell genome to occur. Any convenient protocol for introducing the vector into the target cell may be employed.

Suitable protocols include: calcium phosphate mediated transfection; protoplast fusion, in which protoplasts harboring amplified amounts of vector are fused with the target cell; electroporation, in which a brief high voltage electric pulse is applied to the target cell to render the cell membrane of the target cell permeable to the vector; microinjection, in which the vector is injected directly into the cell, as described in Capechhi et al, Cell (1980) 22: 479; and the like. The above in vitro protocols are well known in the art and are reviewed in greater detail in Sambrook, Fritsch & Maniatis, Molecular Cloning: A Laboratory Manual (Cold Spring Harbor Laboratory Press)(1989) pp 16.30-16.55.

In certain embodiments, e.g., where direct introduction into the target *Listeria* cell does not provide optimal results, one representative method that may be employed is a conjugation method, which comprises: (a) introducing the vector into a non-*Listeria* host cell, e.g., *E. coli*; followed by (b) transfer of the vector from the non-*Listeria* host cell to the *Listeria* host cell, e.g., by conjugation. Introduction into the non-*Listeria* host cell may be accomplished using any of the protocols described above. For the conjugation step, any convenient protocol may be employed, where suitable protocols typically include combining the donor and acceptor cells in a suitable medium and maintaining under suitable conditions for conjugation and vector transfer to occur. Specific representative conditions are provided in the Experimental section below.

The above methods result in stable integration of the vector and any expression cassette carried thereby, e.g., that encodes a heterologous protein/foreign antigen, into a target *Listeria* cell genome in a site specific manner. The subject methods find use with a wide variety of different *Listeria* species.

Utility

The above described vectors and methods of using the same find use in a variety of different applications, where representative applications include, but are not limited to: (a) research applications; (b) vaccine preparation applications; (c) *Listeria* delivery vehicle preparation applications; and the like.

One type of application in which the subject vectors and methods of using may be employed is in research of *Listeria* species. For example, the subject vectors and methods allow simple and efficient strain construction and are widely useful in various strains used to study the intracellular life cycle of *L. monocytogenes*. Additionally, the subject vectors and methods may be employed to produce stable merodiploid strains to allow refined copy number studies and studies of interactions within a protein through multimerization and testing of the dominance or recessive nature of different alleles of a gene in the same bacterial strain.

The subject vectors and methods also find use in vaccine preparation applications. For example, the subject vectors find use in the production of *Listeria* cultures capable of expressing a heterologous antigen, i.e., *Listeria* vaccines, where the *Listeria* cells employed may be attenuated. The attenuated strains employed may be capable of normal invasion of a host cell, but incapable of normal survival or growth in the cell or cell-to-cell spread, or they may have other alterations that preclude normal pathogenicity.

The vaccines produced using vectors of the present invention are administered to a vertebrate by contacting the vertebrate with a sublethal dose of the genetically engineered *Listeria* vaccine, where contact typically includes administering the vaccine to the host. Thus the present invention provides for vaccines genetically engineered with the integration vector and provided in a pharmaceutically acceptable formulation. Administration can be oral, parenteral, intranasal, intramuscular, intravascular, direct vaccination of lymph nodes, administration by catheter or any one or more of a variety of well-known administration routes. In farm animals, for example, the vaccine may be administered orally by incorporation of the vaccine in feed or liquid (such as water). It may be supplied as a lyophilized powder, as a frozen formulation or as a component of a capsule, or any other convenient, pharmaceutically acceptable formulation that preserves the antigenicity of the vaccine. Any one of a number of well known pharmaceutically acceptable diluents or excipients may be employed in the vaccines of the invention. Suitable diluents include, for example, sterile, distilled water, saline, phosphate buffered solution, and the like. The amount of the diluent may vary widely, as those skilled in the art will recognize. Suitable excipients are also well known to those skilled in the art and may be selected, for example, from A. Wade and P. J. Weller, eds., *Handbook of Pharmaceutical Excipients* (1994) The Pharmaceutical Press: London. The dosage administered may be dependent upon the age, health and weight of the patient, the type of patient, and the existence of concurrent treatment, if any. The vaccines can be employed in dosage forms such as capsules, liquid solutions, suspensions, or elixirs, for oral administration, or sterile liquid for formulations such as solutions or suspensions for parenteral, intranasal intramuscular, or intravascular use. In accordance with the invention, the vaccine may be employed, in combination with a pharmaceutically acceptable diluent, as a vaccine composition, useful in immunizing a patient against infection from a selected organism or virus or with respect to a tumor, etc. Immunizing a patient means providing the patient with at least some degree of therapeutic or prophylactic immunity against selected pathogens, cancerous cells, etc.

The subject vaccines prepared with the subject vectors find use in methods for eliciting or boosting a helper T cell or a cytotoxic T-cell response to a selected agent, e.g., pathogenic organism, tumor, etc., in a vertebrate, where such methods include administering an effective amount of the *Listeria* vaccine. The subject vaccines prepared with the subject vectors find use in methods for eliciting in a vertebrate an innate immune response that augments the antigen-specific immune response. Furthermore, the vaccines of the present invention may be used for treatment post-exposure or post diagnosis. In general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure. As such, the subject vaccines prepared with the subject vectors find use as both prophylactic and therapeutic vaccines to induce immune responses that are specific for antigens that are relevant to various disease conditions.

The patient may be any human and non-human animal susceptible to infection with the selected organism. The subject vaccines will find particular use with vertebrates such as man, and with domestic animals. Domestic animals include domestic fowl, bovine, porcine, ovine, equine, caprine, Leporidate (such as rabbits), or other animal which may be held in captivity.

In general, the subject vectors and methods find use in the production of vaccines as described U.S. Pat. No. 5,830,702, the disclosure of which is herein incorporated by reference; as well as PCT publication no WO 99/25376, the disclosures of the priority applications of which are herein incorporated by reference.

The subject vectors also find use in the production of listerial delivery vehicles for delivery of macromolecules to target cells, e.g., as described in: PCT publication no. WO 00/09733 (the priority application of which is herein incorporated by reference); and Dietrich et al., Nature Biotechnology (1998) 16: 181-185. A variety of different types of macromolecules may be delivered, including, but not limited to: nucleic acids, polypeptides/proteins, etc., as described in these publications.

Kits & Systems

Also provided are kits and systems that find use in preparing the subject vectors and/or preparing recombinant *Listeria* cells using the subject vectors and methods, as described above. For example, kits and systems for producing the subject vectors may include one or more of: an initial vector with a multiple cloning site; a restriction endonuclease for cleaving a site in the multiple cloning site, a vector including an expression cassette of interest which is to be inserted into the multiple cloning site; etc. Where the kits and systems are designed for the production of the recombinant *Listeria* cells, the kits and systems may include vectors, or components for making the same, as described above, *Listeria* target cells, non-*Listeria* host cells, and the like. The subject kits may further include other components that find use in the subject methods, e.g., reaction buffers, growth mediums, etc.

The various reagent components of the kits may be present in separate containers, or may all be precombined into a reagent mixture for combination with template DNA.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Materials and Methods

A. Construction of pPL1 Integration Vector.

Standard molecular techniques were used in the construction of the 6101 bp integration vector pPL1 (FIG. 1A). The complete sequence of the pPL1 vector is provided as SEQ ID NO:25. pPL1 is a low copy plasmid that replicates autonomously in *E. coli* and integrates in a site-specific manner in *L. monocytogenes,* and was assembled from 6 independent DNA sources as follows. Restriction sites in the PCR primers used for construction are underlined. All PCR reactions used in cloning steps utilized Vent DNA polymerase (New England Biolabs).

The multiple cloning site (MCS) from pBluescript KS- (Alting-Mees, M. A., and J. M. Short. 1989. pBluescript II: gene mapping vectors. Nucleic Acids Res. 17:9494.) (bp 1-171) was cloned after PCR with primers 5'-G GACGTCATTMCCCTCACTAAAGG-3' and 5'-G GACGTCAATACGACTCACTATAGG-3' (SEQ ID NOS: 01 & 02). The low copy Gram-negative origin of replication and chloramphenicol acetyltransferase (CAT) gene from pACYC184 (Chang, A. C., and S. N. Cohen. 1978. Construction and characterization of amplifiable multicopy DNA cloning vehicles derived from the P15A cryptic miniplasmid. J. Bacteriol. 134:1141-1156.) (bp 172-2253) were cloned after PCR with primers 5'-G GACGTCGCTATTTAACGACCCTGC-3' and 5'-GAG CTGCAGGAGAATTACAACTTATATCGTATGGGG-3' (SEQ ID NOS: 03 & 04). For direct conjugation from *E. coli* to *L. monocytogenes,* the RP4 origin of transfer (oriT) (Pansegrau, W., E. Lanka, P. T. Barth, D. H. Figurski, D. G. Guiney, D. Haas, D. R. Helinski, H. Schwab, V. A. Stanisich, and C. M. Thomas. 1994. Complete nucleotide sequence of Birmingham IncP alpha plasmids. Compilation and comparative analysis. J. Mol. Biol. 239:623-663) (bp 2254-2624) was cloned from plasmid pCTC3 (Williams, D. R., D. I. Young, and M. Young. 1990. Conjugative plasmid transfer from *Escherichia coli* to *Clostridium acetobutylicum.* J. Gen. Microbiol. 136:819-826) after PCR with primers 5'-GCA CTGCAGCCGCTTGCCCTCATCTGTTACGCC-3' and 5'-CATGCATGCCTCTCGCCTGTCCCCTCAGTTCAG-3' (SEQ ID NOS: 05 & 06). The listeriophage U153 integrase gene and attachment site (attPP') (A. Nolte, P. Lauer, and R. Calendar, unpublished; bp 2629-4127)(SEQ ID NO: 25 includes the sequences for these sites), that direct the site-specific integration of the plasmid were cloned after PCR with primers 5'-GT AGATCTTAACTTTCCATGCGAGAGGAG-3' arid 5'-GG GCATGCGATAAAAAGCAATCTATAGAAAAACAGG-3' (SEQ ID NOS: 07 & -08). For expression of the U153 integrase gene, the *L. monocytogenes* p60 promoter (Lauer, P., J. A. Theriot, J. Skoble, M. D. Welch, and D. A. Portnoy. 2001. Systematic mutational analysis of the amino-terminal domain of the *Listeria monocytogenes* ActA protein reveals novel functions in actin-based motility. Mol. Microbiol. 42:1163-1177.) was PCR amplified with primers 5'-CCT AAGCTTTCGATCATCATAATTCTGTC-3' and 5'-GG GCATGCAGATCTTTTTTTCAGAAAATCCCAGTACG-3' (SEQ ID NOS: 09 & 10) and cloned upstream of the integrase gene. Base pairs 4570-6101 are a Hind III-Aat II restriction fragment subcloned from pUC18-Cat (a kind gift from Nancy Freitag), and contain the inducible Gram-positive CAT gene from pC194 (Horinouchi, S., and B. Weisblum. 1982. Nucleotide sequence and functional map of pC194, a plasmid that specifies inducible chloramphenicol resistance. J. Bacteriol. 150:815-825) (bp 4788-5850).

B. Cloning of the hly and actA Genes into pPL1.

The hly gene was subcloned from the plasmid pDP-906 (Jones, S., and D. A. Portnoy. 1994. Characterization of *Listeria monocytogenes* pathogenesis in a strain expressing perfringolysin O in place of listeriolysin O. Infect. Immun. 62(12):5608-5613.) by restriction digestion with BamH I and Xba I, gel purifying a 2.9 kb fragment and by ligating it into pPL1 cut with BamH I and Spe I. The resultant plasmid was designated pPL24 (FIG. 1A). The actA gene was PCR amplified from 10403S genomic DNA with primers 5'-GG TCTAGATCAAGCACATACCTAG-3' and 5'-CG GGATCCTGAAGCTTGGGAAGCAG-3'(SEQ ID NOS: 11 & 12). The 2220 bp PCR product was gel purified, cut with BamH I and Xba I, and cloned into pPL1 cut with BamH I and Spe I. The resultant plasmid was designated pPL25 (FIG. 1A).

C. Phage Curing, Conjugation and Molecular Confirmation of Plasmid Integration.

Phage curing was accomplished by adapting historical methodologies (Cohen, D. 1959. A variant of Phage P2 Originating in *Escherichia coli*, strain B. Virology 7:112-126; Six, E. 1960. Prophage substitution and curing in lysogenic cells superinfected with hetero-immune phage. J. Bacteriol. 80:728-729.). *L. monocytogenes* 10403S derivatives carrying a prophage at comK-attBB' (integrated in the comK ORF as described (Loessner, M. J., R. B. Inman, P. Lauer, and R. Calendar. 2000. Complete nucleotide sequence, molecular analysis and genome structure of bacteriophage A118 of *Listeria monocytogenes*: implications for phage evolution. Mol. Microbiol. 35(2):324-340.)) were grown in BHI at 37° C. to $10^8$ CFU/ml and infected with listeriophage U153 (Hodgson, D. A. 2000. Generalized transduction of serotype 1/2 and serotype 4b strains of *Listeria monocytogenes*. Mol. Microbiol. 35(2):312-323.) at a multiplicity of infection of 20:1 in the presence of 5 mM $CaCl_2$. Cultures were incubated by shaking at 37° C. for 75 minutes and inhibition of growth was monitored by comparison of the $OD_{600}$ of the infected culture with an uninfected control culture. The infected culture was diluted $10^{-2}$ and $10^{-4}$ in BHI, and both dilutions were grown at 37° C. until the $10^{-2}$ dilution had increased 100-fold in optical density. The $10^{-4}$ fold dilution was then diluted $10^{-2}$, and 3 µl were plated on BHI. Fifty colonies were tested for phage release initially by toothpicking colonies into 0.25 ml LB broth and replica plating at 30° C. on a lawn of Mack-4R (DP-L862), a non-lysogenic rough strain of *L. monocytogenes* particularly susceptible to forming plaques. Candidates that did not plaque were then tested by spotting 10 µl of culture on a lawn of Mack-4R to detect plaque formation. If this second test was negative, the candidate was tested whether it could support plaque formation by the phage from the parent 10403S strain (Φ10403, (Hodgson, D. A. 2000. Generalized transduction of serotype 1/2 and serotype 4b strains of *Listeria monocytogenes*. Mol. Microbiol. 35(2): 312-323.)). Curing was confirmed molecularly by PCR with the comK-attBB' specific primer pair PL60/PL61 (sequences follow) for the absence of a phage at comK-attBB'. Approximately 10% of colonies were cured using this procedure.

Recipient strains of *L. monocytogenes* (SLCC-5764, DP-L1169 and DP-L1172) were made streptomycin resistant for counter-selection in conjugation experiments by plate selection on BHI supplemented with 200 µg/ml antibiotic.

pPL1 plasmid constructs were electroporated into *E. coli* strain SM10 (Simon, R., U. Priefer, and A. Pühler. 1983. A broad host range mobilization system for in vitro genetic engineering: transposon mutagenesis in Gram negative bacteria. Bio/Technology 1:784-791.) using standard techniques (Sambrook, J., T. Maniatis, and E. F. Fritsch. 1989. Molecular Cloning: A Laboratory Manual, 2nd edn. ed. Cold Spring Harbor Laboratory Press, Cold Spring Harbor, N.Y.). Bacterial strains were grown to mid-log ($OD_{600}$~0.55) shaking at 30° C. *E. coli* donor strains were grown in LB containing 25 µg/ml of chloramphenicol, *L. monocytogenes* recipient strains were grown in BHI. 2.5 ml of donor culture was mixed with 1.5 ml of recipient culture and filtered onto pre-washed 47 mm 0.45 µm HA type filers (Millipore). The filter was washed once with 10 ml BHI, transferred to a BHI plate with no antibiotics and incubated for 2 hours at 30° C. The bacterial cells were gently resuspended in 2.5 ml of BHI and 25 µl and 50 µl aliquots were plated in 3 ml of LB top agar on BHI plates supplemented with 7.5 µg/ml chloramphenicol and 200 µg/ml streptomycin. Plates were incubated at 30° C. overnight and shifted to 37° C. for 2-3 days. Individual colonies were picked and screened by PCR for integration at the phage attachment site using the primers PL14 (5'-CTCATGAAC-TAGAAAAATGTGG-3') (SEQ ID NO:13), PL60 (5'-TGAAGTAAACCCGCACACGATG-3')(SEQ ID NO:14) and PL61 (5'-TGTAACATGGAGGATCTGGCAATC-3') (SEQ ID NO:15). PCR reactions were performed on small portions of individual bacterial colonies picked with sterile P200 pipet tips from BHI plates directly into 20 µl PCR reactions. The primer pair PL14/PL61 specifically amplifies attBP' in a PCR reaction, resulting in a 743 bp product on integrated strains (both prophage and pPL1 derivatives). The primer pair PL60/PL61 specifically amplifies comK-attBB' in a PCR reaction, resulting in a 417 bp product only on non-lysogenic strains (i.e. DP-L4056). PCR assays were performed in a Hybaid Omn-E thermocycler with an annealing temperature of 55° C. for 30 cycles. Integrants arose at a frequency of approximately $2 \times 10^{-4}$ per donor cell.

D. Hemolysis on Blood Plates and Hemolytic Activity Assay.

Hemolysis on blood plates was scored on tryptic soy agar plates supplemented with 5% defimbrinated sheep blood (HemoStat, Davis Calif.). Hemolytic assays were performed essentially as described (Portnoy, D. A., P. S. Jacks, and D. J. Hinrichs. 1988. Role of hemolysin for the intracellular growth of Listeria monocytogenes. J. Exp. Med. 167(4): 1459-1471.). Hemolytic activity is expressed as the reciprocal of the dilution of culture supernatant required to lyse 50% of sheep erythrocytes.

E. Plaquing in L2 Cells.

Plaque sizes were determined as previously described (Lauer, P., J. A. Theriot, J. Skoble, M. D. Welch, and D. A. Portnoy. 2001. Systematic mutational analysis of the amino-terminal domain of the Listeria monocytogenes ActA protein reveals novel functions in actin-based motility. Mol. Microbiol. 42(5):1163-1177.). Each strain was plaqued in 6 to 8 independent experiments and compared to 10403S in each experiment.

F. SDS-PAGE of Surface Expressed ActA.

Surface expressed ActA protein was prepared from late-log phase bacterial cultures grown in LB broth ($OD_{600}$~0.7) by resuspending equivalent amounts in SDS-PAGE buffer and boiling for 5 min. which extracts surface-expressed proteins but does not perturb the cell wall. Equivalent amounts were loaded on 7% SDS-PAGE and visualized with Coomassie blue.

G. Xenopus laevis Cell Extract Motility Assays.

X. laevis egg cytoplasmic extract was prepared as described (Theriot, J. A., J. Rosenblatt, D. A. Portnoy, P. J. Goldschmidt-Clermont, and T. J. Mitchison. 1994. Involvement of profilin in the actin-based motility of L. monocytogenes in cells and in cell-free extracts. Cell 76(3):505-517.) and supplemented with tetramethylrhodamine iodoacetamide-labeled actin (Theriot, J. A., and D. C. Fung. 1998. Listeria monocytogenes-based assays for actin assembly factors. Methods Enzymol. 298:114-122.). SLCC-5764-derived strains were grown overnight to stationary phase, washed 1×, added to cell extracts and incubated for 45 minutes before microscopic observation.

H. $LD_{50}$ Determinations.

Limited $LD_{50}$ were performed in BALB/c mice as described (Portnoy, D. A., P. S. Jacks, and D. J. Hinrichs. 1988. Role of hemolysin for the intracellular growth of Listeria monocytogenes. J. Exp. Med. 167(4):1459-1471.). Animal experiments were performed in the laboratory of Archie Bouwer at Oregon Health Sciences Center, Portland, Oreg.

I. Identification of the PSA Attachment Site and Construction of pPL2.

The PSA attachment site (tRNA$^{Arg}$-attBB') DNA sequence was obtained through a combination of inverse PCR and genome walking. Inverse PCR was performed on Sau3 AI-digested DP-L4061 DNA (WSLC 1042 lysogenic for PSA) (SEQ ID NO:26 is the sequence of 2,072 bp surrounding WSLC 1042 tRNA$^{Arg}$-attBB') using the divergent primers PL95 (5'-ACATAATCAGTCCAAAGTAGATGC)(SEQ ID NO:16) and PL97 (5'-ACGAATGTAAATATTGAGCGG) (SEQ ID NO:17) that anneal within the PSA int gene. The resultant DNA sequence was used to design further oligonucleotides and these were used with the Genome Walker kit (Clontech), per the manufacturer's recommendations. DNA sequence and tRNA analysis was done with using MacVector (Accelrys), DNAsis (Hitachi), BLAST algorithm (2), and tRNAscan-SE (Lowe, T. M., and S. R. Eddy. 1997. tRNAscan-SE: a program for improved detection of transfer RNA genes in genomic sequence. Nucleic Acids Res. 25(5): 955-964.).

pPL1 was modified to utilize a different attachment site on the L. monocytogenes chromosome by replacing the U153 integrase gene and attachment site in the plasmid. The PSA int and attPP' were PCR amplified from PSA genomic DNA with primers PL100 (5'-GAAGATCTCCAAAAATAAACAGGTGGTGG) (SEQ ID NO:18) and PL101 (5'-CATGCATGCGTGGAGGGAAAGAAGAACGC) (SEQ ID NO:19) with Vent DNA polymerase, digested with Bgl II and Sph I, and ligated to pPL1 that had been digested with the same enzymes. The resultant plasmid was designated pPL2 (FIG. 1B). The sequence of pPL2 is provided as SEQ ID NO:28.

The DNA sequence of the PSA tRNA$^{Arg}$-attBB' from serotype 1/2 L. monocytogenes strains was obtained by a plasmid-trap strategy. DP-L4211 (pPL2 integrated in 10403S) genomic DNA was digested with Nsi I and Nhe I, which do not cleave in the vector, and ligated under dilute conditions to promote self-ligation. The ligations were transformed into XL1-blue and chloramphenicol resistant colonies were selected. The plasmids obtained were sequenced with the convergent primers PL94 (5'-GGAGGGAAAGAAGAACGC) (SEQ ID NO:20) and PL95 (sequence above) for attPB' and attBP', respectively, which flank attPP' in the PSA genomic DNA sequence. Further, because of the divergence between the sequences downstream of the tRNA$^{Arg}$ gene among serotypes, a serotype 1/2 specific PCR assay across tRNA$^{Arg}$-attBB' was developed from the 10403S DNA sequence and used to determine the prophage status of various L. monocytogenes strains. Primers PL102 (5'-TATCAGACCTAACCCAAACCTTCC) (SEQ ID NO:21) and PL103 (5'-AATCGCAAAATAAAAATCTTCTCG) (SEQ ID NO:22) specifically amplify a 533 bp PCR product in non-lysogenic serotype 1/2 strains. The primer pair NC16 (5'-GTCAAAACATACGCTCTTATC)(SEQ ID NO:23) and PL95 specifically amplify a 499 bp PCR product in strains that are either lysogenic or contain an integration vector at tRNA$^{Arg}$-attBB'. (SEQ ID NO:27 provides the 643 bp surrounding 10403S tRNA$^{Arg}$-attBB')

II. Results and Discussion

A. pPL1 Forms Stable, Single-copy Integrants in Various L. monocytogenes Strains.

pPL1 is the first shuttle integration vector that we constructed to facilitate strain construction in L. monocytogenes. In order to test the pPL1 vector, we needed a L. monocytogenes strain that did not have a phage at the comK bacterial attachment site. We adapted historical methods to cure L. monocytogenes strains of their prophages and found after superinfection with phage U153, which has the same attachment site as the endogenous 10403S prophage, we were able to isolate prophage-free strains (see Materials and Methods). The prophage-cured 10403S strain was designated DP-L4056 and was used in subsequent experiments.

Conjugation was chosen as a method for introducing the vector into the target cells, as many Listeria spp. are inefficiently transformed. Conjugation of pPL1 from E. coli into L. monocytogenes was successful. Drug resistant transconjugants arose at a reproducible frequency of ~2×10$^{-4}$ per donor E. coli cell, approximately three-fold lower than conjugation with autonomously replicating plasmids, indicating ~30% integration efficiency for strains receiving the plasmid by conjugation. All chloramphenicol resistant colonies were positive with the PCR assay using primers PL14 and PL61 and negative using a PCR assay across attPP' in pPL1 (PL14 paired with a primer in the RP4 oriT) indicating that they were true integrants and that the full genetic complement of plasmid pPL1 had integrated into the Listeria chromosome. In addition, this experiment demonstrated that pPL1 was not maintained as an episomal plasmid and that the vector did not integrate as a concatamer.

We tested the stability of the integrants under non-selective growth conditions. Three integrant strains, DP-L4074 and the merodiploid strains DP-L4076 and DP-L4078 (described in the following sections) were passed in liquid BHI media for 100 generations and plated for single colonies. Ninety-six colonies were then exposed to 0.1 µg/ml chloramphenicol (to induce CAT gene expression) and patched on plates containing 7.5 µg/ml antibiotic. All colonies retained drug resistance. Thirty colonies from each non-selective growth experiment were assayed with the PL14/PL61 PCR assay and all PCR reactions resulted in the 743 bp product, indicating all transconjugants retained the integrated plasmid.

We further addressed whether the integration vector would be generally useful for any L. monocytogenes strain with an available attachment site. There have been greater than 320 listeriophages isolated, and many have restricted host ranges. It was unclear whether there was a biological barrier to U153 integrase gene function in host strains that do not support U153 infection. We therefore picked three strains that did not contain a prophage at the comK attachment site; two serotype 4b clinical isolates and SLCC-5764, a serotype 1/2a strain that constitutively expresses the known virulence factors in an unregulated manner and has been useful for studying these virulence factors in vitro. Each of these strains was first made streptomycin resistant for counter selection in conjugation experiments (as described in Materials and Methods). Streptomycin resistant derivatives were chosen on the basis of having the same growth rate as the parent strain to avoid experimental complications related to viability. The resultant strains, DP-L4088, DP-L4089, and DP-L4082 all proved suitable recipients for pPL1 integration at a similar frequency to DP-L4056.

Finally, we conducted a survey of L. monocytogenes isolates to identify suitable strains that do not harbor a prophage at the comK attachment site using the PCR assays across comK-attBB' (primers PL60/PL61) and the hybrid attPB' (primers PL14/PL61). The results of these experiments (Table 2) indicated many of the strains commonly used to study the biology and pathogenesis of L. monocytogenes including 10403S, L028, and EGDe had a prophage at comK.

TABLE 2

Prophage status of various strains

| Strain | Description | Source | serotype | PL60/PL61 comK | PL14/PL61 attPB' |
|---|---|---|---|---|---|
| 10403S | wild type | rabbit pellets | 1/2a | −[a] | + |
| DP-L4056 | 10403S phage cured | This work | 1/2a | +[b] | − |
| DP-L861 | SLCC-5764 (Mack) | WT (overexpresser) | 1/2a | + | − |
| DP-L3818 | WSLC 1118::A118 | Camembert cheese | 4b | − | + |
| DP-L3633 | EGDe | WT (1960s human) | 1/2a | − | + |
| DP-L3293 | LO28 | WT (clinical origin) | 1/2c | − | + |
| DP-L185 | F2397 | L.A., Jalisco cheese | 4b | + | − |
| DP-L186 | ScottA | Massachusettes outbreak, milk | 4b | + | − |
| DP-L188 | ATTC 19113 | Denmark, human | 3 | + | − |
| DP-L1168 | clinical | cole slaw | 4b | + | − |
| DP-L1169 | clinical | patient | 4b | + | − |
| DP-L1170 | clinical | patient | 4b | + | − |
| DP-L1171 | clinical | brie | 1/2b | + | − |
| DP-L1172 | clinical | alfalfa tablets | 4b | + | − |
| DP-L1173 | clinical | deceased patient | 4b | − | + |
| DP-L1174 | clinical | deceased patient | 4b | − | + |
| DP-L3809 | 1981 Halifax | placenta | 4b | + | − |
| DP-L3810 | 1981 Halifax | CSF & brain | 4b | + | − |
| DP-L3812 | 1981 Halifax | coleslaw | 4b | + | − |
| DP-L3813 | 1996 Halifax | blood | ? | − | + |
| DP-L3814 | 1981 Halifax | CSF | 4b | + | − |
| DP-L3815 | 1993 Halifax | CSF | 1/2a | + | − |
| DP-L3816 | 1995 Halifax | blood | ? | + | − |
| DP-L3817 | 1993 Halifax | CSF | 1/2a | + | − |
| DP-L3862 | 1998 Michigan | patient | 4b | − | + |

[a](−): negative PCR result for primer pair noted at top of column.
[b](+): positive PCR result for primer pair noted at top of column. The PL60/PL61 primer pair specifically amplify a 417 bp PCR product in non-lysogenic strains and result in no PCR product in lysogenic strains. The PL14/PL61 primer pair specifically amplify a 743 bp PCR product in lysogenic strains and result in no PCR product in non-lysogenic strains.

B. The Status of comK did not Affect the Virulence of *L. monocytogenes*.

We next compared DP-L4056 and DP-L4074 to wild-type 10403S in standard virulence assays to determine if the presence of a prophage at comK, lack of prophage, or integration vector altered the virulence phenotypes. These three strains were assayed for LLO activity, ability to form plaques in monolayers of L2 cells, and for virulence in the mouse $LD_{50}$ assay (Table 3). All were indistinguishable from one another, strongly suggesting that the integrity of the comK ORF and the presence of pPL1 had no measurable impact on virulence.

absolutely required for bacterial pathogenesis as mutants in actA are both unable to spread from cell-to-cell and form a plaque in a cell monolayer and are 3 logs less virulent than wild type. Additionally, ActA expression appears to be more complex than that of LLO: there are two promoters that drive actA expression. One is immediately upstream of the actA ORF and the second is in front of the mpl gene upstream of actA.

We constructed several strains to evaluate the complementation of actA at the phage attachment site. The first group

TABLE 3

Complementation of actA and hly

| Strain | Genotype | Hemolysis on blood plates | Hemolytic activity[a] | Plaque size[b] | $LD_{50}$[c] |
|---|---|---|---|---|---|
| 10403S | wild type | + | nd | 100 (na) | ~2 × 10$^4$ |
| DP-L4056 | 10403S phage cured | + | 97 | 101 (1.4) | <1 × 10$^5$ |
| DP-L4074 | DP-L4056 comK::pPL1 | + | 98 | 99 (1.4) | <1 × 10$^5$ |
| DP-L4027 | DP-L2161 phage cured, Δhly | − | 0 | 0 (0) | 1 × 10$^8$ |
| DP-L4075 | DP-L4027 Δhly, comK::pPL24 | + | 99 | 97 (3.9) | <1 × 10$^5$ |
| DP-L4076 | DP-L4056 comK::pPL24 | + | 198 | 96 (2) | nd |
| DP-L4029 | DP-L3078 phage cured, ΔactA | nd | nd | 0 (0) | 2 × 10$^7$ |
| DP-L4077 | DP-L4029 ΔactA, comK::pPL25 | nd | nd | 86 (4) | <1 × 10$^5$ |
| DP-L4078 | DP-L4056 comK::pPL25 | nd | nd | 72 (6.8) | nd |

[a]Hemolytic units data shown is from one representative experiment.
nd: not determined.
[b]Plaque size is the average of 8 to 10 independent experiments and shown as a percent of wild type (defined as 100%). Standard deviations are shown in parentheses. na: not applicable.
[c]$LD_{50}$s of 10403S and Δhly (DP-L2161) were determined in (37), the $LD_{50}$ of the ΔactA strain (DP-L1942, a smaller deletion within the actA ORF that does not support actin nucleation at the bacterial surface) was determined in (4).

C. Full Complementation of hly at the Phage Attachment Site.

Listeriolysin-O (LLO), the gene product of hly, is a secreted pore-forming cytolysin that is responsible for escape from the membrane-bound vacuole when *L. monocytogenes* first enters a host cell. LLO is absolutely required for the intracellular life cycle of *L. monocytogenes* and virulence. LLO activity can be measured by hemolytic activity on red blood cells. Hly mutants fail to form plaques in monolayers of L2 cells and are 5 logs less virulent in the mouse $LD_{50}$ assay.

We cloned the hly structural gene into pPL1 and conjugated this plasmid from *E. coli* to phage-cured wild type and Δhly *L. monocytogenes* derivatives, resulting in DP-L4076 (an hly merodiploid) and DP-L4075 (hly only at the phage comK-att site). These strains were tested for hemolytic activity on blood plates, for the relative amount of hemolytic units secreted, ability to form a plaque in a monolayer of L2 cells, and virulence in the mouse $LD_{50}$ assay (Table 3). The quantitative complementation of hly in the deletion strain background and the doubling of hemolytic units produced in the merodiploid strain indicate two things. First, gene expression is not de facto affected by ectopic expression at the comK chromosomal position. Second, the hly promoter is self-contained. Additionally, a two-fold increase in the amount of LLO is not deleterious to the virulence and intracellular life cycle of *L. monocytogenes*, at least as measured by plaquing.

D. Complementation of actA at the Phage Attachment Site Approaches Wild-type Expression.

ActA, a second major *L. monocytogenes* virulence factor, is responsible for commandeering host cell actin-cytoskeletal factors used for intracellular bacterial motility. ActA is also included making second-site complemented (DP-L4077) and merodiploid (DP-L4078) strains in the 10403S background. These were assayed for plaque formation in an L2 monolayer (Table 3). Integrated ActA did not fully complement in this assay (plaque size of 86%) and the merodiploid strain formed an even smaller plaque (72% of wild type). We interpret these results to indicate that there may be a small contribution of the second promoter upstream of the mpl gene for optimal actA expression. Additionally, there appears to be a critical concentration of ActA on the surface of intracellular bacteria because two copies of actA (with 3 promoters driving expression) further decreases the ability to spread from cell to cell, presumably because there is too much ActA on the bacterial surface for optimal motility.

Figure 3:
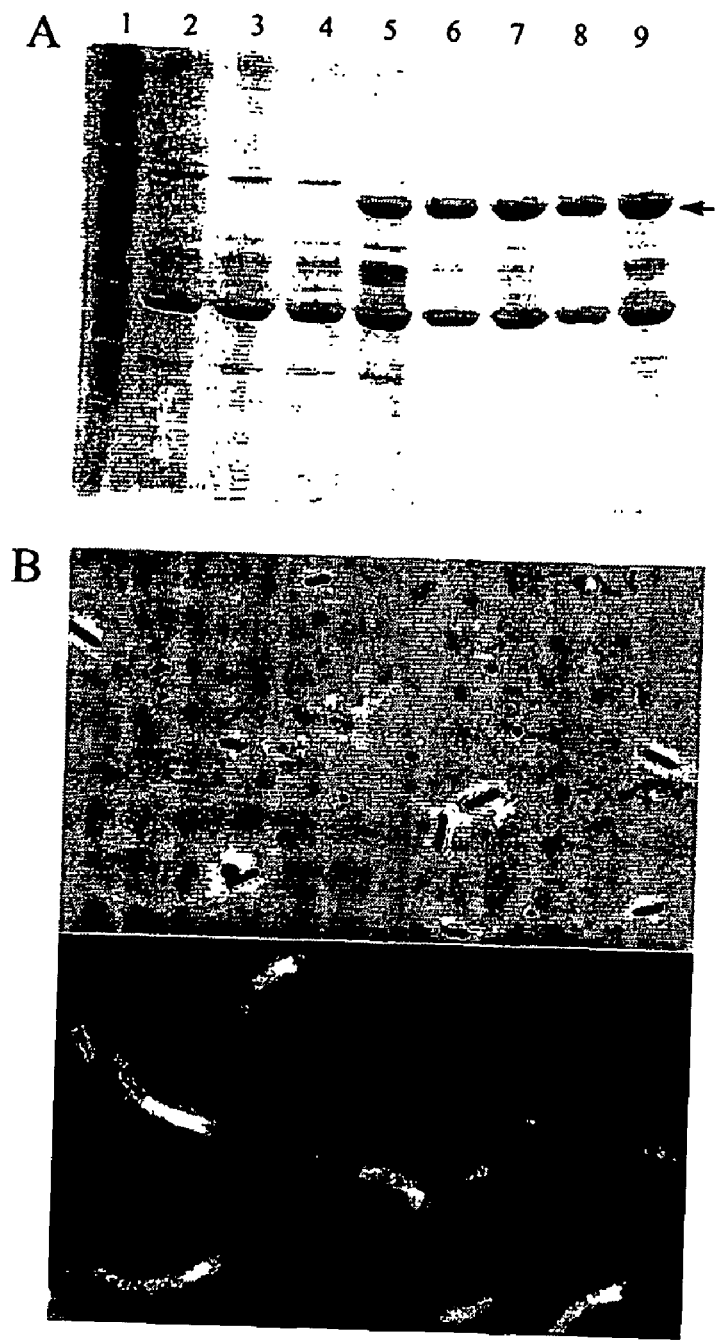
FIG. 3. Expression and functional complementation of ActA in SLCC-5764. (A) Coomassie blue stained SDS-PAGE of SLCC-5764 derived strains grown to late-log phase. ActA is indicated by an arrow. Lane 1: molecular size marker; lane 2: DP-L3780; lane 3: DP-L4083; lane 4: DP-L4086; lane 5: SLCC-5764; lane 6: DP-L4082; lane 7: DP-L4084; lane 8: DP-L4085; lane 9: DP-L4087. Strains are described in Table 1. (B) Actin tail formation and movement of DP-L4087 in Xenopus cell extract. The top panel is a phase image; the bottom panel is a fluorescent image of the same field.
Figure 4:
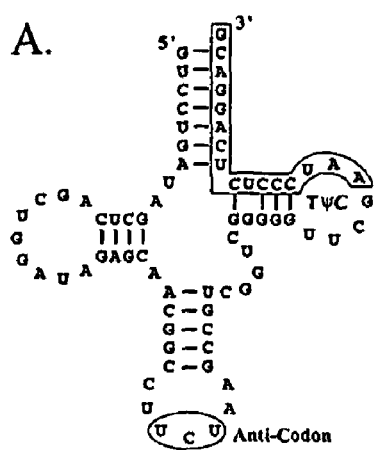
FIG. 4. (A) Clover-leaf diagram of tRNA$^{Arg}$ utilized as the PSA attachment site. The arginine anticodon is circled. The region with sequence identity between the tRNA gene and the PSA attPP' is outlined. The boundaries of the tRNA$^{Arg}$ gene and Cove score (82.37) were predicted with tRNAscan-SE (31). (B) Alignment of the tRNA$^{Arg}$-attBB' region of *L. monocytogenes* WSLC 1042 (top line) and the attPP' region of PSA downstream of the integrase gene. The 74 nt tRNA$^{Arg}$ gene of *L. monocytogenes* is boxed and the 17 bp overlapping region of sequence identity (core integration site) is shaded grey. The tRNA$^{Arg}$ gene anticodon is shown in bold and underlined. Identical nucleotide residues are indicated by (:). The numbers located at the left indicate the nucleotide position in the DNA sequences of the WSLC 1042 attachment site (AJ314913) and PSA genome (AJ312240).

We further tested ActA complementation in the virulence gene over-expressing strain SLCC-5764. ActA is effectively expressed in this strain from the comK-attBB' site (FIG. 3A, lane 9). Considering the plaquing data of 10403S complemented actA strains, it may have been predicted that the merodiploid strain DP-L4085 would make more ActA than the parent strain. However, this was not observed: the parent strain, the complemented strain and the merodiploid strain all expressed similar levels of ActA (FIG. 3A, lanes 5, 8, and 9). This observation was likely due to the complete lack of regulation and high level of constitutive expression of ActA in SLCC-5764. Additionally, DP-L4087. supports actin nucleation at the bacterial surface, actin tail formation and bacterial motility in cell extracts (FIG. 3B). The results of these cell-extract experiments indicate that the integration vector system for complementation will be useful for in vitro studies of L. monocytogenes motility, facilitating strain construction and placing various molecular constructs in different host strains for study in a desired set of assays. In particular, several alleles of actA that have unusual motility phenotypes have been transferred to the SLCC-5764 ΔactA strain using pPL1 and are currently being evaluated in cell extracts. The study of these mutants in the simplified cell-extract system should yield insights into the activities of poorly understood regions of the ActA protein.

The stains referenced above are provided in the following Table 1

| Strain | Relevant genotype or plasmid |
|---|---|
| *E. coli*: | |
| SM10 | Conjugation donor. F-thi-1 thr-1 leuB6 recA tonA21 lacY1 supE44 Mu + Cl− [RP4-2(Tc::Mu)] $Km^r$ Tra+ |
| XL1-Blue | Plasmid manipulations. recA1 endA1 gyrA96 thi-1 hsdR17 supE44 relA1 lac [F'proAB $lacI^qZ$ ΔM15 Tn10 ($Tet^r$)] |
| DP-E4067 | Integration vector pPL1/SM10 |
| DP-E4068 | hly integration vector pPL24/SM10 |
| DP-E4069 | actA integration vector pPL25/SM10 |
| DP-E4190 | Integration vector pPL2/SM10 |
| *L. monocytogenes*: | |
| 10403S | wild type |
| DP-L4056 | 10403S phage cured |
| DP-L4027 | DP-L2161 phage cured, Δhly |
| DP-L4029 | DP-L3078 phage cured, ΔactA |
| DP-L4074 | DP-L4056 comK::pPL1 |
| DP-L4075 | DP-L4027 Δhly, comK::pPL24 |
| DP-L4076 | DP-L4056 comK::pPL24 |
| DP-L4077 | DP-L4029 ΔactA, comK::pPL25 |
| DP-L4078 | DP-L4056 comK::pPL25 |
| SLCC-5764 | Virulence gene over expresser (Mack, DP-L861) |
| DP-L862 | Mack-4R (SLCC-5764 rough isolate) |
| DP-L4082 | SLCC-5764 $Str^r$ derivative |
| DP-L3780 | SLCC-5764 ΔactA (deletion of amino acids 7-633) |
| DP-L4083 | DP-L3780S ($Str^r$ dervivative) |
| DP-L4084 | DP-L4082, comK::pPL1 |
| DP-L4085 | DP-L4082, comK::pPL25 |
| DP-L4086 | DP-L4083, comK::pPL1 |
| DP-L4087 | DP-L4083 ΔactA, comK::actA |
| DP-L4088 | DP-L1169S 4b strain, $Str^r$ |
| DP-L4089 | DP-L1172S 4b strain, $Str^r$ |
| DP-L4090 | DP-L4088, comK::pPL1 |
| DP-L4091 | DP-L4089, comK::pPL1 |
| DP-L4199 | EGDe, $Str^r$ derivative |
| DP-L4026 | WSLC 1042, (ATCC 23074) |
| DP-L4061 | WSLC 1042::PSA |
| DP-L4221 | 10403S, $tRNA^{Arg}$::pPL2 |

E. Phage PSA Integrates into a $tRNA^{Arg}$ gene and pPL2 Construction.

pPL1 integration into *L. monocytogenes* strains that harbour a prophage in the comK attachment site is hindered by the process of first having to cure the prophage from the host strain. To alleviate the need for the phage-curing step, the specificity of pPL1 integration was changed to that of the PSA prophage. PSA, (Phage from ScottA) is the prophage of *L. monocytogenes* strain ScottA, a serotype 4b strain that was isolated during an epidemic of human listeriosis. Using the PSA genomic DNA sequence, we identified an integrase-like ORF with a contiguous non-coding sequence that we predicted to contain the attPP' sequences. The PSA integrase sequence was then used to obtain the DNA sequence of PSA-attBB' from the PSA lysogenic strain DP-L4061 (see Materials and Methods). PSA was found to integrate in a $tRNA^{Arg}$ gene that is 88% identical to a $tRNA^{Arg}$ gene (trnSL-ARG2) from *B. subtilis*. The anticodon of the $tRNA^{Arg}$ gene is 5'UCU, the most commonly used arginine anticodon in *L. monocytogenes*. The PSA and bacterial attachment sites share 17 bp of DNA identity, and the $tRNA^{Arg}$-attBB' contains a short nucleotide sequence that completes the $tRNA^{Arg}$ sequence that is interrupted by integration of PSA (FIG. 4). The attachment site $tRNA^{Arg}$ gene is present only once in the genome of *L. monocytogenes* strain EGDe and apparently only once in the serotype 4b. This indicates that not only is the PSA integration site unique, but also that precise reconstitution of the gene upon integration (or excision) is likely required for survival of the cell.

pPL2 was constructed by replacing the U153 listeriophage integrase gene and attachment site in pPL1 with the PSA listeriophage integrase gene and attachment site. pPL2 was tranformed into SM10 and the resulting strain was mated into 10403S, EGDe (carrying a streptomycin resistance mutation) and the serotype 4b strain DP-L4088. Chloramphenicol resistant transconjugants arose from each of these crosses at approximately $2\times10^{-4}$ per donor cell, the same rate as pPL1 integration. Two recombinants from each cross were restreaked under drug selection and tested by PCR for the presence of PSA-attBP' using primers NC16 and PL95. The expected 499 bp PCR product was obtained in each of the colonies tested, indicating pPL2 integrates into $tRNA^{Arg}$-attBB' in both serotype 1/2 and 4b strains. We tested the stability of the integrated pPL2 in both EGDe and DP-L4088 strains with the same non-selective 100-generation experiment described for pPL1. Forty-nine colonies from each of the amplified cultures were tested for chloramphenicol resistance. The EGDe-derived strains retained 100% drug resistant colonies indicating complete stability of the integrants. In the case of the DP-L4088 integrant, two of the 49 colonies were chloramphenicol sensitive, suggesting a low level of excision can occur in this serotype 4b strain. In order to test whether precise excision had occured, we PCR amplified across $tRNA^{Arg}$-attBB' and sequenced the PCR products. The wild-type DNA sequence was obtained, indicating a precise excision event.

During the course of our PCR experiments, we noted a divergence between the $tRNA^{Arg}$-attPB' sites from serotype 4b and serotype 1/2 *L. monocytogenes*. To determine nature of this divergence, we isolated and sequenced the $tRNA^{Arg}$-attBB' site from 10403S (as described in Materials and Methods). We found that the sequence of attPB' in 10403S (3' of the $tRNA^{Arg}$ gene) is unrelated to that of the serotype 4b strain WSLC 1042. In contrast to this, the sequence of attBP' (5' of the $tRNA^{Arg}$ gene) in 10403S is 96-97% identical to the corresponding regions in *L. monocytogenes* serotype 4b strain WSLC 1042, the serotype 4b strain sequenced by TIGR, and the serotype 1/2a strain EGDe sequenced by the European *Listeria* Consortium. Thus, the bacterial attBB' sequences recognized by the PSA integrase are likely to encompass more of the attB DNA sequence than the attB' DNA sequence. Additionally, we tested the availability of the $tRNA^{Arg}$-attBB' in the common laboratory strains of *L. monocytogenes* with a PCR assay using primers PL102 and PL103. We found the $tRNA^{Arg}$ attachment site to be available in strains 10403S, EGEe, and L028 indicating that pPL2 may be readily utilized in these backgrounds for strain construction, complementation, and genetics studies without first curing endogenous prophages.

F. Expression of *Aquoria victoria* GFP.

A GFP coding sequence as described in U.S. Pat. No. 5,777,079 (the disclosure of which is herein incorporated by reference), is cloned into plasmid pPL1, transferred into the genome of *L. monocytogenes*. The GFP coding sequence is amplified by polymerase chain reaction (PCR) and the PCR fragment is cloned into the multiple cloning site of pPL1. A suitable promoter, containing appropriate transcriptional elements and a translational leader sequence for expressing the GFP in *L. monocytogenes* are cloned at the 5' end of the GFP coding sequence such that they induce the expression of the GFP protein. The modified pPL1 plasmid constructs are electroporated into *E. coli* strain SM10 using standard techniques, and the modified pPL1 plasmid construct is conjugated into *L. monocytogenes* as described above. Recombinant *L. monocytogenes* are selected on BHI plates supplemented with 7.5 µg/ml chloramphenicol and 200 µg/ml streptomycin. Individual colonies are picked and screened by PCR for integration at the phage attachment site using the primers PL14 (5'-CTCATGAACTAGAAAAATGTGG-3') (SEQ ID NO:13), PL60 (5'-TGAAGTAAACCCGCACACGATG-3') (SEQ ID NO:14) and PL61 (5'-TGTAACATGGAGGT-TCTGGCAATC-3')(SEQ ID NO:15). Cultures of recombinant *L. monocytogenes* are grown, prepared and screened for GFP.

III. Utility of pPL1 and pPL2.

The construction and characterization of the first single step site specific integration vectors for use in *L. monocytogenes* furthers the genetic tools available for the study of this pathogen. These vectors allow more facile strain construction than historic methods and are widely useful in various strains used to study the intracellular life cycle of *L. monocytogenes*. Additionally, stable merodiploid strains can be constructed to allow refined copy number studies and studies of interactions within a protein through multimerization and testing of the dominance or recessive nature of different alleles of a gene in the same bacterial strain.

pPL1 and pPL2 are also useful for vaccine development, e.g., for at least enhancing, including both eliciting and boosting, an immune response to a target cells or cells, e.g., a foreign pathogen, etc. Several recombinant *L. monocytogenes* systems have been used to elicit cell-mediated immune responses in mice (Frankel, F. R., S. Hegde, J. Lieberman, and Y. Paterson. 1995. Induction of cell-mediated immune responses to human immunodeficiency virus type 1 Gag protein by using *Listeria monocytogenes* as a live vaccine vector. J. Immunol. 155(10):4775-4782.; Goossens, P. L., G. Milon, P. Cossart, and M. F. Saron. 1995. Attenuated *Listeria monocytogenes* as a live vector for induction of CD8+ T cells in vivo: a study with the nucleoprotein of the lymphocytic choriomeningitis virus. Int. Immunol. 7(5):797-805; Ikonomidis, G., Y. Paterson, F. J. Kos, and D. A. Portnoy. 1994. Delivery of a viral antigen to the class I processing and presentation pathway by *Listeria monocytogenes*. J. Exp. Med. 180(6): 2209-2218.; Shen, H., M. K. Slifka, M. Matloubian, E. R. Jensen, R. Ahmed, and J. F. Miller. 1995. Recombinant *Listeria monocytogenes* as a live vaccine vehicle for the induction of protective anti-viral cell-mediated immunity. Proc. Natl. Acad. Sci. USA 92(9):3987-3991.). One limitation with plasmid-based expression of recombinant proteins in *L. monocytogenes* is the stability of the plasmids in vivo (i.e. in the host animal) without selection. Additionally, chromosomal construction of strains expressing foreign antigens is time consuming. pPL1 and pPL2 alleviate both of these concerns.

It is evident from the above results and discussion that subject invention provides a number of advantages. The construction and characterization of the first single step site specific integration vectors for use in *L. monocytogenes* as described herein furthers the genetic tools available for the study of this pathogen. For example, the subject vectors and methods allow more facile strain construction than historic methods and are widely useful in various strains used to study the intracellular life cycle of *L. monocytogenes*. Furthermore, the subject invention provides important new tools for the production of vaccine preparations. One limitation with plasmid-based expression of recombinant proteins in *L. monocytogenes* is the stability of the plasmids in vivo (i.e. in the host animal) without selection. Additionally, chromosomal construction of strains expressing foreign antigens is time consuming. The subject vectors and methods of use alleviate both of these concerns. As such, the present invention represents a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of eliciting or boosting a cellular immune response to an antigen in a subject, said method comprising: administering to said subject an effective amount of Listeria cells that express said antigen, wherein said cells are transformed with an integration vector capable of integrase mediated site-specific Listeria genome integration, wherein said integration vector comprises a listeriophage attachment site and a nucleic acid sequence encoding a listeriophage integrase.

2. The method according to claim 1, wherein said Listeria cells are attenuated.

3. The method according to claim 1, wherein said integration vector is a plasmid.

4. The method according to claim 3, wherein said attachment site provides for integration at an integration site selected from the group consisting of: the comK integration site and the tRNA$^{Arg}$ integration site.

5. The method according to claim 1, wherein said integration vector further includes a multiple cloning site.

6. The method according to claim 5, wherein said integration vector further includes a coding sequence.

7. The method according to claim 6, wherein said coding sequence encodes a polypeptide.

8. The method according to claim 7, wherein said polypeptide is said antigen.

9. The method according to claim 1, wherein said integration vector is pPL1.

10. The method according to claim 1, wherein said integration vector is pPL2.

* * * * *

SEQUENCE LISTING

<160> NUMBER OF SEQ ID NOS: 28

<210> SEQ ID NO 1
<211> LENGTH: 25
<212> TYPE: DNA

```
<213> ORGANISM: Artificial Sequence
<220> FEATURE:
<223> OTHER INFORMATION: oligonucleotide

<400> SEQUENCE: 1
ggacgtcatt aaccctcact aaagg                                         25

<210> SEQ ID NO 2
<211> LENGTH: 25
<212> TYPE: DNA
<213> ORGANISM: Artificial Sequence
<220> FEATURE:
<223> OTHER INFORMATION: oligonucleotide

<400> SEQUENCE: 2
ggacgtcaat acgactcact atagg                                         25

<210> SEQ ID NO 3
<211> LENGTH: 25
<212> TYPE: DNA
<213> ORGANISM: Artificial Sequence
<220> FEATURE:
<223> OTHER INFORMATION: oligonucleotide

<400> SEQUENCE: 3
ggacgtcgct atttaacgac cctgc                                         25

<210> SEQ ID NO 4
<211> LENGTH: 36
<212> TYPE: DNA
<213> ORGANISM: Artificial Sequence
<220> FEATURE:
<223> OTHER INFORMATION: oligonucleotide

<400> SEQUENCE: 4
gagctgcagg agaattacaa cttatatcgt atgggg                             36

<210> SEQ ID NO 5
<211> LENGTH: 33
<212> TYPE: DNA
<213> ORGANISM: Artificial Sequence
<220> FEATURE:
<223> OTHER INFORMATION: oligonucleotide

<400> SEQUENCE: 5
gcactgcagc cgcttgccct catctgttac gcc                                33

<210> SEQ ID NO 6
<211> LENGTH: 33
<212> TYPE: DNA
<213> ORGANISM: Artificial Sequence
<220> FEATURE:
<223> OTHER INFORMATION: oligonucleotide

<400> SEQUENCE: 6
catgcatgcc tctcgcctgt cccctcagtt cag                                33

<210> SEQ ID NO 7
<211> LENGTH: 29
<212> TYPE: DNA
<213> ORGANISM: Artificial Sequence
<220> FEATURE:
<223> OTHER INFORMATION: oligonucleotide

<400> SEQUENCE: 7
gtagatctta actttccatg cgagaggag                                     29
```

<210> SEQ ID NO 8
<211> LENGTH: 36
<212> TYPE: DNA
<213> ORGANISM: Artificial Sequence
<220> FEATURE:
<223> OTHER INFORMATION: oligonucleotide

<400> SEQUENCE: 8
gggcatgcga taaaaagcaa tctatagaaa aacagg                          36

<210> SEQ ID NO 9
<211> LENGTH: 29
<212> TYPE: DNA
<213> ORGANISM: Artificial Sequence
<220> FEATURE:
<223> OTHER INFORMATION: oligonucleotide

<400> SEQUENCE: 9
cctaagcttt cgatcatcat aattctgtc                                  29

<210> SEQ ID NO 10
<211> LENGTH: 37
<212> TYPE: DNA
<213> ORGANISM: Artificial Sequence
<220> FEATURE:
<223> OTHER INFORMATION: oligonucleotide

<400> SEQUENCE: 10
gggcatgcag atctttttttt cagaaaatcc cagtacg                        37

<210> SEQ ID NO 11
<211> LENGTH: 24
<212> TYPE: DNA
<213> ORGANISM: Artificial Sequence
<220> FEATURE:
<223> OTHER INFORMATION: oligonucleotide

<400> SEQUENCE: 11
ggtctagatc aagcacatac ctag                                       24

<210> SEQ ID NO 12
<211> LENGTH: 25
<212> TYPE: DNA
<213> ORGANISM: Artificial Sequence
<220> FEATURE:
<223> OTHER INFORMATION: oligonucleotide

<400> SEQUENCE: 12
cgggatcctg aagcttggga agcag                                      25

<210> SEQ ID NO 13
<211> LENGTH: 22
<212> TYPE: DNA
<213> ORGANISM: Artificial Sequence
<220> FEATURE:
<223> OTHER INFORMATION: oligonucleotide

<400> SEQUENCE: 13
ctcatgaact agaaaaatgt gg                                         22

<210> SEQ ID NO 14
<211> LENGTH: 22
<212> TYPE: DNA
<213> ORGANISM: Artificial Sequence
<220> FEATURE:

<223> OTHER INFORMATION: oligonucleotide

<400> SEQUENCE: 14
tgaagtaaac ccgcacacga tg                                      22

<210> SEQ ID NO 15
<211> LENGTH: 24
<212> TYPE: DNA
<213> ORGANISM: Artificial Sequence
<220> FEATURE:
<223> OTHER INFORMATION: oligonucleotide

<400> SEQUENCE: 15
tgtaacatgg aggttctggc aatc                                    24

<210> SEQ ID NO 16
<211> LENGTH: 24
<212> TYPE: DNA
<213> ORGANISM: Artificial Sequence
<220> FEATURE:
<223> OTHER INFORMATION: oligonucleotide

<400> SEQUENCE: 16
acataatcag tccaaagtag atgc                                    24

<210> SEQ ID NO 17
<211> LENGTH: 21
<212> TYPE: DNA
<213> ORGANISM: Artificial Sequence
<220> FEATURE:
<223> OTHER INFORMATION: oligonucleotide

<400> SEQUENCE: 17
acgaatgtaa atattgagcg g                                       21

<210> SEQ ID NO 18
<211> LENGTH: 29
<212> TYPE: DNA
<213> ORGANISM: Artificial Sequence
<220> FEATURE:
<223> OTHER INFORMATION: oligonucleotide

<400> SEQUENCE: 18
gaagatctcc aaaaataaac aggtggtgg                               29

<210> SEQ ID NO 19
<211> LENGTH: 29
<212> TYPE: DNA
<213> ORGANISM: Artificial Sequence
<220> FEATURE:
<223> OTHER INFORMATION: oligonucleotide

<400> SEQUENCE: 19
catgcatgcg tggagggaaa gaagaacgc                               29

<210> SEQ ID NO 20
<211> LENGTH: 18
<212> TYPE: DNA
<213> ORGANISM: Artificial Sequence
<220> FEATURE:
<223> OTHER INFORMATION: oligonucleotide

<400> SEQUENCE: 20
ggagggaaag aagaacgc                                           18

```
<210> SEQ ID NO 21
<211> LENGTH: 24
<212> TYPE: DNA
<213> ORGANISM: Artificial Sequence
<220> FEATURE:
<223> OTHER INFORMATION: oligonucleotide

<400> SEQUENCE: 21
tatcagacct aacccaaacc ttcc                                                24

<210> SEQ ID NO 22
<211> LENGTH: 24
<212> TYPE: DNA
<213> ORGANISM: Artificial Sequence
<220> FEATURE:
<223> OTHER INFORMATION: oligonucleotide

<400> SEQUENCE: 22
aatcgcaaaa taaaaatctt ctcg                                                24

<210> SEQ ID NO 23
<211> LENGTH: 21
<212> TYPE: DNA
<213> ORGANISM: Artificial Sequence
<220> FEATURE:
<223> OTHER INFORMATION: oligonucleotide

<400> SEQUENCE: 23
gtcaaaacat acgctcttat c                                                   21

<210> SEQ ID NO 24
<211> LENGTH: 6101
<212> TYPE: DNA
<213> ORGANISM: Shuttle integration vector pPL1
<220> FEATURE:
<221> NAME/KEY: misc_feature
<222> LOCATION: 3676
<223> OTHER INFORMATION: n = A,T,C or G

<400> SEQUENCE: 24
gacgtcaata cgactcacta tagggcgaat tgggtaccgg gccccccctc gaggtcgacg          60
gtatcgataa gcttgatatc gaattcctgc agcccggggg atccactagt tctagagcgg         120
ccgccaccgc ggtggagctc cagcttttgt tccctttagt gagggttaat gacgtcgcta         180
tttaacgacc ctgccctgaa ccgacgaccg ggtcgaattt gctttcgaat ttctgccatt         240
catccgctta ttatcactta ttcaggcgta gcaccaggcg tttaagggca ccaataactg         300
ccttaaaaaa attacgcccc gccctgccac tcatcgcagt actgttgtaa ttcattaagc         360
attctgccga catggaagcc atcacagacg gcatgatgaa cctgaatcgc cagcggcatc         420
agcaccttgt cgccttgcgt ataatatttg cccatggtga aaacgggggc gaagaagttg         480
tccatattgg ccacgtttaa atcaaaactg gtgaaactca cccagggatt ggctgagacg         540
aaaaacatat tctcaataaa ccctttaggg aataggccag gttttcacc gtaacacgcc          600 acatcttgcg aatatatgtg tagaaactgc cggaaatcgt cgtggtattc actccagagc         660
gatgaaaacg tttcagtttg ctcatggaaa acggtgtaac aagggtgaac actatcccat         720
atcaccagct caccgtcttt cattgccata cggaattccg gatgagcatt catcaggcgg         780
gcaagaatgt gaataaaggc cggataaaac ttgtgcttat ttttctttac ggtctttaaa         840
aaggccgtaa tatccagctg aacggtctgg ttataggtac attgagcaac tgactgaaat         900
gcctcaaaat gttctttacg atgccattgg gatatatcaa cggtggtata tccagtgatt         960
```

```
tttttctcca ttttagcttc cttagctcct gaaaatctcg ataactcaaa aaatacgccc    1020
ggtagtgatc ttatttcatt atggtgaaag ttggaacctc ttacgtgccg atcaacgtct    1080
cattttcgcc aaaagttggc ccagggcttc ccggtatcaa cagggacacc aggatttatt    1140
tattctgcga agtgatcttc cgtcacaggt atttattcgg cgcaaagtgc gtcgggtgat    1200
gctgccaact tactgattta gtgtatgatg gtgtttttga ggtgctccag tggcttctgt    1260
ttctatcagc tgtccctcct gttcagctac tgacggggtg gtgcgtaacg gcaaaagcac    1320
cgccggacat cagcgctagc ggagtgtata ctggcttact atgttggcac tgatgagggt    1380
gtcagtgaag tgcttcatgt ggcaggagaa aaaaggctgc accggtgcgt cagcagaata    1440
tgtgatacag gatatattcc gcttcctcgc tcactgactc gctacgctcg gtcgttcgac    1500
tgcggcgagc ggaaatggct tacgaacggg gcggagattt cctggaagat gccaggaaga    1560
tacttaacag ggaagtgaga gggccgcggc aaagccgttt ttccataggc tccgccccc    1620 tgacaagcat cacgaaatct gacgctcaaa tcagtggtgg cgaaacccga caggactata    1680
aagataccag gcgtttcccc ctggcggctc cctcgtgcgc tctcctgttc ctgcctttcg    1740
gtttaccggt gtcattccgc tgttatggcc gcgtttgtct cattccacgc ctgacactca    1800
gttccgggta ggcagttcgc tccaagctgg actgtatgca cgaaccccc gttcagtccg    1860 accgctgcgc cttatccggt aactatcgtc ttgagtccaa cccggaaaga catgcaaaag    1920
caccactggc agcagccact ggtaattgat ttagaggagt tagtcttgaa gtcatgcgcc    1980
ggttaaggct aaactgaaag gacaagtttt ggtgactgcg ctcctccaag ccagttacct    2040
cggttcaaag agttggtagc tcagagaacc ttcgaaaaac cgccctgcaa ggcggttttt    2100
tcgttttcag agcaagagat tacgcgcaga ccaaaacgat ctcaagaaga tcatcttatt    2160
aatcagataa aatatttcta gatttcagtg caatttatct cttcaaatgt agcacctgaa    2220
gtcagcccca tacgatataa gttgtaattc tccgccgctt gccctcatct gttacgccgg    2280
cggtagccgg ccagcctcgc agagcaggat tcccgttgag caccgccagg tgcgaataag    2340
ggacagtgaa gaaggaacac ccgctcgcgg gtgggcctac ttcacctatc ctgcccggct    2400
gacgccgttg gatacaccaa ggaaagtcta cacgaaccct ttggcaaaat cctgtatatc    2460
gtgcgaaaaa ggatggatat accgaaaaaa tcgctataat gaccccgaag cagggttatg    2520
cagcggaaaa gcgctgcttc cctgctgttt tgtggaatat ctaccgactg gaaacaggca    2580
aatgcaggaa attactgaac tgaggggaca ggcgagaggc atgcgataaa aagcaatcta    2640
tagaaaaaca ggttactttt tatttataat tttagtttct cgattcgttt ccgtccaacg    2700
agagaaaacg aggaactaaa caatctaaat aaacaagcta ctagagccat tcaatagtaa    2760
cttgttcacc gtcaatataa attttattaa ttagtgattt taaataaagt tgcttttctc    2820
ggaactctaa agagtcaaaa tcaactgttg ctaaatcagc taaattttct tgtatctttt    2880 tattttctt caattcttcg ttagcttcta tttgtgcttc ataataatta atttgagcat    2940
cgatatcagc catcatagca tcaagttctg aaacttcgta agaaccgctg atatataaat    3000
caaatagccg tttctttttt acgtgttctg ttttaagttt ttcatttaag ctatctaatt    3060
cgtcttcttt atctacattc ctagaagcga aactatagtt attcacgcga tcaataatta    3120
attcctcgag tttgtcagct ctccaaattt tatttccaca ttttctagt tcatgagtat    3180 gtttgtaagt cttgcaacta taatatctat aatgatattt ttttccgcgg gaaacagtat    3240
cttttctccg atgaacaaaa cccaacccac attttccaca cactaccaaa ttatttagca    3300
acgatgctga atctctattc atatttggat ttttacccat gcgagaaaaa atttcttgaa    3360
```

```
ctcgataaaa ttgttcctct gaaataatag gctcatgaac accttttgta tgcactttat   3420
ccgcataaga tacataacca cagtataaat cattagttag ccaattgttg taactgctat   3480
atgatttcac tttgaatcct aattttttta gtctcttctg taaagtggta atgctttttt   3540
cttcctcaaa aatatcataa atcatttgta attgttttgc ttcttcttca ttaatatata   3600
atttagtatc tataacatca tagccgaatg ttctaccttt tgcagtcgtt aaaggaagac   3660
ctgcttcaat acgctnaatt ttccccatca ccatacgatc acgtatagtt tcgcgctcta   3720
attgagcaaa tacggataat ataccaatca tcgcgcgccc aaatgggcta gaggtgtcaa   3780
gagtttcaga caaactaaca aattctacat tgtttttttaa gaagtattct tcaataagcg   3840
ttatcgtatc tctttgtgag cgggaaagtc tatctaagcg atatacaaca acagcatcaa   3900
tttcatgtaa tttacttagc atttcattta gtgcggggcg attcatgttt gaaccgctgt   3960
atccgccgtc tatgaaaata tcgtatacgt cccaatcctt cgagcggcac aaggctgtta   4020
gcttttcagt ttgagcttgt atagagtaat tctctatttg ttcttgagta gatacgcgta   4080
tataaatagc tgccttcatt tccgttctcc tctcgcatgg aaagttaaga tctttttttc   4140
agaaaatccc agtacgtaat taagtatttg agaattaatt ttatattgat taatactaag   4200
tttacccagt tttcacctaa aaaacaaatg atgagataat aactccaaag gctaaagagg   4260
actataccaa ctatttgtaa taattctgta acagttgaaa agcgaacgtg tattcttagg   4320
gcttgagatg tactgctggg taaacccttta tagtgtaagt gggatgtgaa cgttaatcaa   4380
caactttcgc tatgggaaac ctattgtttt ttgttaatag aaaaacttaa tacatttgta   4440
atataaaaac cggcagtttt tccgttcttc gtgactcgaa atgaattgcc agatgagttt   4500
atggtattct ataatagaag gtatggagga tgttatataa tgagacagaa ttatgatgat   4560
cgaaagctag cttggcactg gccgtcgttt tacaacgtcg tgactgggaa accctggcg   4620
ttacccaact taatcgcctt gcagcacatc ccccttttcgc cagctggcgt aatagcgaag   4680
aggcccgcac cgatcgccct tcccaacagt tgcgcagcct gaatggcgaa tggcgcctga   4740
tgcggtattt tctccttacg catctgtgcg gtatttcaca ccgcatatca aatggttcgg   4800
atctggagct gtaatataaa aaccttcttc aactaacggg gcaggttagt gacattagaa   4860
aaccgactgt aaaagtaca gtcggcatta tctcatatta taaaagccag tcattaggcc   4920
tatctgacaa ttcctgaata gagttcataa acaatcctgc atgataacca tcacaaacag   4980
aatgatgtac ctgtaaagat agcggtaaat atattgaatt accttatta atgaattttc   5040
ctgctgtaat aatgggtaga aggtaattac tattattatt gatatttaag ttaaacccag   5100
taaatgaagt ccatggaata atagaaagag aaaaagcatt ttcaggtata ggtgttttgg   5160
gaaacaattt ccccgaacca ttatatttct ctacatcaga aaggtataaa tcataaaact   5220
ctttgaagtc attctttaca ggagtccaaa taccagagaa tgttttagat acaccatcaa   5280
aaattgtata aagtggctct aacttatccc aataacctaa ctctccgtcg ctattgtaac   5340
cagttctaaa agctgtattt gagtttatca cccttgtcac taagaaaata aatgcagggt   5400
aaaatttata tccttcttgt tttatgtttc ggtataaaac actaatatca atttctgtgg   5460
ttatactaaa agtcgtttgt tggttcaaat aatgattaaa tatctctttt ctcttccaat   5520
tgtctaaatc aatttttatta aagttcattt gatatgcctc ctaaattttt atctaaagtg   5580
aatttaggag gcttacttgt ctgctttctt cattagaatc aatcctttt taaaagtcaa   5640
tattactgta acataaatat atattttaaa aatatcccac tttatccaat tttcgtttgt   5700
```

-continued

| | |
|---|---|
| tgaactaatg ggtgctttag ttgaagaata aagaccacat taaaaaatgt ggtcttttgt | 5760 |
| gttttttaa aggatttgag cgtagcgaaa atcctttc tttcttatct tgataataag | 5820 |
| ggtaactatt gcccagatcc gaaccatttg atatggtgca ctctcagtac aatctgctct | 5880 |
| gatgccgcat agttaagcca gccccgacac ccgccaacac ccgctgacgc gccctgacgg | 5940 |
| gcttgtctgc tcccggcatc cgcttacaga caagctgtga ccgtctccgg gagctgcatg | 6000 |
| tgtcagaggt tttcaccgtc atcaccgaaa cgcgcgagac gaaagggcct cgtgatacgc | 6060 |
| ctatttttat aggttaatgt catgataata atggtttctt a | 6101 |

<210> SEQ ID NO 25
<211> LENGTH: 3897
<212> TYPE: DNA
<213> ORGANISM: Bacteriophage U153
<220> FEATURE:
<221> NAME/KEY: misc_feature
<222> LOCATION: 695
<223> OTHER INFORMATION: n = A,T,C or G

<400> SEQUENCE: 25

| | |
|---|---|
| aagctttaaa gaaattcaag aagaaacatc ggtaactagc cataaattaa ccaaagttct | 60 |
| aatctcgctt gaagagaaca aactgattga aaaaattgga caatctagag caacaaaata | 120 |
| caaattaatt gaatctacag aggaatatct aaccaatctt caacacacat ttcgaaaaat | 180 |
| tgttcaattt tatgttgaaa atgataaata aaaatatgaa tgttttttta tttgttagta | 240 |
| gtgtaacttt ccatgcgaga ggagaacgga atgaaggca gctatttata tacgcgtatc | 300 |
| tactcaagaa caaatagaga attactctat acaagctcaa actgaaaagc taacagcctt | 360 |
| gtgccgctcg aaggattggg acgtatcga tattttcata gacggcggat acagcggttc | 420 |
| aaacatgaat cgccccgcac taaatgaaat gctaagtaaa ttacatgaaa ttgatgctgt | 480 |
| tgttgtatat cgcttagata gactttcccg ctcacaaaga gatacgataa cgcttattga | 540 |
| agaatacttc ttaaaaaaca atgtagaatt tgttagtttg tctgaaactc ttgacacctc | 600 |
| tagcccattt gggcgcgcga tgattggtat attatccgta tttgctcaat tagagcgcga | 660 |
| aactatacgt gatcgtatgg tgatggggaa aattnagcgt attgaagcag gtcttccttt | 720 |
| aacgactgca aaaggtagaa cattcggcta tgatgttata gatactaaat tatatattaa | 780 |
| tgaagaagaa gcaaaacaat tacaaatgat ttatgatatt tttgaggaag aaaaaagcat | 840 |
| taccactta cagaagagac taaaaaaatt aggattcaaa gtgaaatcat atagcagtta | 900 |
| caacaattgg ctaactaatg atttatactg tggttatgta tcttatgcgg ataaagtgca | 960 |
| tacaaaaggt gttcatgagc ctattatttc agaggaacaa ttttatcgag ttcaagaaat | 1020 |
| tttttctcgc atgggtaaaa atccaaatat gaatagagat tcagcatcgt tgctaaataa | 1080 |
| tttggtagtg tgtggaaaat gtgggttggg ttttgttcat cggagaaaag atactgtttc | 1140 |
| ccgcggaaaa aatatcatt atagatatta tagttgcaag acttacaaac atactcatga | 1200 |
| actagaaaaa tgtggaaata aaatttggag agctgacaaa ctcgaggaat taattattga | 1260 |
| tcgcgtgaat aactatagtt tcgcttctag gaatgtagat aaagaagacg aattagatag | 1320 |
| cttaaatgaa aaacttaaaa cagaacacgt aaaaaagaaa cggctatttg atttatatat | 1380 |
| cagcggttct tacgaagttt cagaacttga tgctatgatg gctgatatcg atgctcaaat | 1440 |
| taattattat gaagcacaaa tagaagctaa cgaagaattg aagaaaaata aaaagataca | 1500 |
| agaaaattta gctgatttag caacagttga ttttgactct ttagagttcc gagaaaagca | 1560 |
| acttttattta aaatcactaa ttaataaaat ttatattgac ggtgaacaag ttactattga | 1620 |

```
atggctctag tagcttgttt atttagattg tttagttcct cgttttctct cgttggacgg   1680
aaacgaatcg agaaactaaa attataaata aaaagtaacc tgttttttcta tagattgctt   1740
tttatcaatt atatagaaga aagccgcttt ttattagatt ataattgatg ttttttgatt   1800
tatatttcac tccctgtgca aataatgata taacagcaac ctcgaacttt ttagttcggg   1860
gtattttttt gaaattaatt tataaaaaca cttgcaatta taatacat gtattataat   1920
ataaatatag aaaggagttg agaaagtgaa agacatctta gaggaaataa aaacagtcct   1980
tgaaattgta actcttgcag tagcgctgat aacattacgc aagatagaca aaaacaagga   2040
caagtaacca gagggggtgaa actcccctcc ctctataaaa gtatatcacg tcttttcataa   2100
attatgaata aatatatctg ggttatatta attgttatat gcgttaacgg actcgctagt   2160
tactttcaga acacagcatt gaccatcatt gctatactga ctacattagc ttgttttagta   2220
tatttaataa aaataggaa gtgattaatt atgacgaaaa aaacgacctc tgacgcgcag   2280
ttgaaagcaa ataaggaatg gcaaagcaag aacaaagaac atgcaaacta tttaaaaatct   2340
cgttcagctg cgcgttcttt tataaagaat aaagctacgt tggaagattt gaaggaactt   2400
gaaaaattaa ttatagaggg aaaaattaat cataagggaa tgattaagga taaatgatgc   2460
acgctaagca catgcttggc gttttttgca taaaaaagc cctaacgttg aagttaggga   2520
ctgacatata taaaaaatag aagttgacaa ctttaaggcg actaccacga caggcagctt   2580
acaagctatg actagccttg actaatcatt tatgcgacac tcaaagaatt attatctaac   2640
ttcttaatca agaataacaa aaatcaaaca agttagcaag tatttcaggc atttttattta   2700
taacaaatat ctagatcaca aaaatgtcgc ggaaaataat ggtcacaacc aatattacat   2760
aaacttaaaa gttctctatt tctcttatca ggttatgtg ctgttacgtg atttctacat   2820
actctaaaaa ctgtattagc gaataagtct acaacttgaa ttaaatcttt attttgtgaa   2880
tcctatatg atgtttcaac agaagagaaa attggatgtt ccattgtaaa tttaatagtt   2940
aaatattctt gtaagctatt taatgattca attgcggtat ttctatcatc tatttgcatt   3000
ttcaaatagt tatttgctgg gttaattggt attttagaaa tttcatttac cgttagataa   3060
ataaaataat taaagacaa agatgtatta ttcaaaagat gattgactag ttggtggtta   3120
tcgactatct taaaatgaaa tttagcatct gattttgttg aaagcatatt aaatattaat   3180
tttttcattt caaaaggcat ctccgaacct tttatctctt ttgtaatatc taacttacta   3240
gatggatacc ttttaagata ttttaatttt gcatctctga actgtctaat tacattatat   3300
ggtttctctg tttctaaaaa agcaataaca aaatatctgt tattaaaatt tttatttta   3360
gttatagttc ctgattcatc tacaaaaagt ctcatcccag ttcctccact tttttactta   3420
aattatatta tactaattaa gtttgaggaa gtggaacgta tgtacttata attcgaagtt   3480
atgaaaaatc cccccatcaa tataaaacaa aaaagccccc gaaataataa tcgagggcat   3540
taaactaaat cttttttaaca aacttcggtg ttagcagtga gatagtaacc agatttcgtt   3600
ttcaagcgag gtgttccgcc ttttgttttc gccattcctg taatcgtgaa gatagtgcct   3660
accggatatg tgccaccggt tttatgcttc tcagtaaagt ctactgaatt gtatagatca   3720
cactgtacta gtgttttaac ttttcgcgga ttttctgtgt agtatgtgtt tttgcttgct   3780
ggtgtgtgtg gttttcctgc ttttaacttc gctaataatg ttgtgttctg cgttgctgtt   3840
cctttataat ccttaattcc gtattgattt gctagttttt tacgattcgc aaagctt   3897
```

<210> SEQ ID NO 26

-continued

<211> LENGTH: 2702
<212> TYPE: DNA
<213> ORGANISM: Listeria monocytogenes

<400> SEQUENCE: 26
gatatcgcgc acgtgaatta aacgcagatt ttgccttttt tggtcacccg catgaactag 60
gagtagacat gctagacgac accatcattt taaacccagg aagcatttcc ttaccaagag 120
gacgcatccg tgtcaaaaca tacgctctta tcgattcaac accagaaggc attcaagttc 180
gattcatgga ccgggacgac aacgaactaa cggacctaac ccaaaccttc ccattaacga 240
agcataacta ggtcaaaaga cacccgaaaa agaaaaaatg caataactta aagaaaacca 300
ttgacaaaca agcgatttaa acataaaatg gtatttggct gttgaaaaaa cagtgccatt 360
tgtcctgata gctcagctgg atagagcaac ggccttctaa gccgtcggtc gggggttcga 420
atccctctca ggacgtaaat agctatatta aagaaatctc taaaacgttg aaaaaccttg 480
atattaaagg ttggatggat gttttagaga ttttttttata tcttataata tctgttttat 540
tccgtatttt tcatgacatt tgtgacaaaa tttgtgctat ttccatccat ttttaatgtg 600
aaaaaagcat ctattttagt ttgattatgt tgatgcaaat tagagcttag attattataa 660
tattttaatg ttattaatat caggttgacc tctcctaagt gttagacatg tttcaccagt 720
ctccatagga gtgtggtagc tgattgcaca gtaattatat actttacgtc aatatcaaaa 780
gcaagtccaa ttaaaatgga ttaccttgcc ccgtaaatga caacttctga aaataggtaa 840
aaggaacaaa agatgatgta attagggtct agtgcatttg tggtgaattt aggttttgat 900
tataatgaga atctccgttt agaggttgtt cttttgaaaa cgatagaagc aattataggt 960
atcgactacc atatattact gaaaaaagag ctagattaaa taaaaaaata attctaacat 1020
cataggaggc aattatgact tttttaaaca ccttaaaatt aaatttggaa aatgaaaaaa 1080
agagaatgtt atccgatgct tttatgaaaa aacaagaagg aatcattgta aactatatag 1140
tgacttgcag taaggattct gctattggca ttagtaaaaa ggcaattgat atattattga 1200
taatcaatga aaatacattt cctgaatggc caaatgtaga tagatggctt tctattttgc 1260
caaaatattt tacggattct ttttcaaaat caaaaaatatt gcatagtgaa gattggctat 1320
ttgaagagtg gttatactgg tttgaacctg aaaatagatt ttggttttta ggagaattag 1380
atcctgttga taatgagcat ttgaaaataa gcatagttgt acaagaacac ccttttccag 1440
tagaatcatt agaagttcta cttatgaagc taggaacaag cgaattacat gaaattggta 1500
tggaatgagg ttaaatgtac ttttaacgga tatatctttt acaatagagc tgaattttgt 1560
tagagtttaa aatgaaaaaa caactaagtt ataacgaaag gagctaacac ttgatggaaa 1620
attacgtgtc aatagtaaaa atcgaaaaca atctttccgt gtgcttttac aacagctcgg 1680
agaaagtagt agcaattgct aagaaaatga atgagattaa cgaagaagct tatatgcatg 1740
gttacaattg ggaagcattt ttcaactact atttacctaa atatgctcca gatgtcttag 1800
aaggaatggg ctctgatccg gaagcgggaa tgtatgtggc gtattacacg ctatcacctg 1860
aaactgaggc acgagcagaa aaacttgttc aagtaattac gaatctcatc gaaaatgaag 1920
aactacttta tcaaataatt gaaaatgaag gcaataatat tagttgggat aattaatcct 1980
ttttctaaaa aatccttatc tatttattcg tatagtatta gcaagaggtg aagaacctgt 2040
ataatataat tgacgatatt ttaaagcatt agatcctatt ggcagatgct cttaaaacgt 2100
taaacagtaa aataaaaaat ctctaaaaca tttgaaaccc tttgtaatta aaaggtgaat 2160
gttttagaga tttttttatc ttgcatttcc catttttatt ccgttgtttt tgtggcaaat 2220

-continued

```
tttattaaaa ctagttcaag taattacgaa tctcattgaa aacgaagaac tactttataa    2280
aatagtcaaa aattaggaca agcagattat tgagatgatt gatcctttac tttaataata    2340 attttatgt aaactcatcc cttattaggt gttctattgt atgacttgag agtagttttt      2400
ttgagaattt caagcaataa atttaaatat attagagagt ctaaaattag cactaatccc    2460
taaaaagata tgaacgatat gtgaacgatg ataccaagaa atgaaaaaat ttctatacta    2520
tattcaaatt gtaagcttgg gactgctata attagtactt attgaggcga tataatgcca    2580
catacattaa atacagaata aactcattct ttaagataat aattacatct aaggagacta    2640
atcatgaaaa gaaagataag ttctatcatt gtagtcggga taatgttctt tcaatcatta    2700
ac                                                                    2702

<210> SEQ ID NO 27
<211> LENGTH: 643
<212> TYPE: DNA
<213> ORGANISM: Listeria monocytogenes

<400> SEQUENCE: 27
agcatttcct taccaagagg gcgcatccgt atcaaaacat acggctctta tcaattcaca     60
ccagaaggca tccaagttcg attcatggac cgagatgaca acgaactatc agacctaacc    120
caaaccttcc cattaacgaa taacgaagca taactaggtc aaaagacacc cgaaaaagaa    180
aaaatgcaat aacttaaaga aaaccattga caaacaagcg atttaaacat aaaatggtat    240
ttggctgttg aaaagacagt gccatttgtc ctgatagctc agctggatag agcaacggcc    300
ttctaagccg tcggtcgggg gttcgaatcc ctctcaggac gtaatatgaa gcgccgtaaa    360
cgttgttaat acaatgttta cggcgctttt tggttttcg aagttcaaat aaagtacaaa     420
aaatttaaat tccattaatc ttttcatta attatatgta attaggcttc taaagtcatt    480
actatagtgt tttggcccaa tcttaatttt gaagaatata atctttaatt ttggtattag    540
tcttatttag tagcatttgc tccataaaaa aatagaaaaa attaatacca gtcttatata    600
aaaatcttct catgacgaga agatttttat tttgcgattg agc                       643

<210> SEQ ID NO 28
<211> LENGTH: 6123
<212> TYPE: DNA
<213> ORGANISM: Shuttle integration vector pPL2

<400> SEQUENCE: 28
gacgtcaata cgactcacta tagggcgaat tgggtaccgg gccccccctc gaggtcgacg     60
gtatcgataa gcttgatatc gaattcctgc agcccggggg atccactagt tctagagcgg    120
ccgccaccgc ggtggagctc cagcttttgt tccctttagt gagggttaat gacgtcgcta    180
tttaacgacc ctgccctgaa ccgacgaccg ggtcgaattt gctttcgaat ttctgccatt    240
catccgctta ttatcactta ttcaggcgta gcaccaggcg tttaagggca ccaataactg    300
ccttaaaaaa attacgcccc gccctgccac tcatcgcagt actgttgtaa ttcattaagc    360
attctgccga catggaagcc atcacagacg gcatgatgaa cctgaatcgc cagcggcatc    420
agcaccttgt cgccttgcgt ataatatttg cccatggtga aacgggggc gaagaagttg    480 tccatattgg ccacgtttaa atcaaaactg gtgaaactca cccagggatt ggctgagacg    540
aaaaacatat tctcaataaa ccctttaggg aataggccca ggttttcacc gtaacacgcc    600
acatcttgcg aatatatgtg tagaaactgc cggaaatcgt cgtggtattc actccagagc    660
```

-continued

```
gatgaaaacg tttcagtttg ctcatggaaa acggtgtaac aagggtgaac actatcccat      720
atcaccagct caccgtcttt cattgccata cggaattccg gatgagcatt catcaggcgg      780
gcaagaatgt gaataaaggc cggataaaac ttgtgcttat ttttctttac ggtctttaaa      840
aaggccgtaa tatccagctg aacggtctgg ttataggtac attgagcaac tgactgaaat      900
gcctcaaaat gttctttacg atgccattgg gatatatcaa cggtggtata tccagtgatt      960
tttttctcca ttttagcttc cttagctcct gaaaatctcg ataactcaaa aaatacgccc     1020
ggtagtgatc ttatttcatt atggtgaaag ttggaacctc ttacgtgccg atcaacgtct     1080
cattttcgcc aaaagttggc ccagggcttc ccggtatcaa cagggacacc aggatttatt     1140
tattctgcga agtgatcttc cgtcacaggt atttattcgg cgcaaagtgc gtcgggtgat     1200
gctgccaact tactgattta gtgtatgatg gtgtttttga ggtgctccag tggcttctgt     1260
ttctatcagc tgtccctcct gttcagctac tgacggggtg gtgcgtaacg gcaaaagcac     1320
cgccggacat cagcgctagc ggagtgtata ctggcttact atgttggcac tgatgagggt     1380
gtcagtgaag tgcttcatgt ggcaggagaa aaaaggctgc accggtgcgt cagcagaata     1440
tgtgatacag gatatattcc gcttcctcgc tcactgactc gctacgctcg gtcgttcgac     1500
tgcggcgagc ggaaatggct tacgaacggg gcggagattt cctggaagat gccaggaaga     1560
tacttaacag ggaagtgaga gggccgcggc aaagccgttt ttccataggc tccgcccccc     1620
tgacaagcat cacgaaatct gacgctcaaa tcagtggtgg cgaaacccga caggactata     1680
aagataccag gcgtttcccc ctggcggctc cctcgtgcgc tctcctgttc ctgcctttcg     1740
gtttaccggt gtcattccgc tgttatggcc gcgtttgtct cattccacgc tgacactca      1800 gttccgggta ggcagttcgc tccaagctgg actgtatgca cgaaccccc gttcagtccg      1860 accgctgcgc cttatccggt aactatcgtc ttgagtccaa cccggaaaga catgcaaaag     1920
caccactggc agcagccact ggtaattgat ttagaggagt tagtcttgaa gtcatgcgcc     1980
ggttaaggct aaactgaaag gacaagtttt ggtgactgcg ctcctccaag ccagttacct     2040
cggttcaaag agttggtagc tcagagaacc ttcgaaaaac cgccctgcaa ggcggttttt     2100
tcgttttcag agcaagagat tacgcgcaga ccaaaacgat ctcaagaaga tcatcttatt     2160
aatcagataa atatttcta gatttcagtg caatttatct cttcaaatgt agcacctgaa      2220
gtcagcccca tacgatataa gttgtaattc tccgccgctt gccctcatct gttacgccgg     2280
cggtagccgg ccagcctcgc agagcaggat tcccgttgag caccgccagg tgcgaataag     2340
ggacagtgaa gaaggaacac ccgctcgcgg gtgggcctac ttcacctatc ctgcccggct     2400
gacgccgttg gatacaccaa ggaaagtcta cacgaaccct ttggcaaaat cctgtatatc     2460
gtgcgaaaaa ggatggatat tccgaaaaaa tcgctataat gaccccgaag cagggttatg     2520
cagcggaaaa gcgctgcttc cctgctgttt tgtggaatat ctaccgactg gaaacaggca     2580
aatgcaggaa attactgaac tgaggggaca ggcgagaggc atgcgtggag ggaaagaaga     2640
acgctgttga aaaatcttc tctggactac ttgaaacaaa agaattaaag tcatttata      2700 aaaaccttga gaaaaacat cttgatataa aaactattta taacgaatat ttatttcaat     2760
gtaataataa ataatattta ttattacata aaatgtttgt ggtattattt gtggtatata     2820
tatcctaaat ggctttatat cagtgtgtgt taatccctct caggacgtta aatagtaatg     2880
taaagaaatc tctaaaacgt tgaaaagcct tgatattaaa gggcggatga atgttttgga     2940 gttttttta tatcgtataa tacccgtttt attccgttgt ttttgtggca tttgtggtaa     3000
aatttgtggt attttcatct gtttttagtg tgaaaaaagc atctactttg gactgattat     3060
```

```
gttgtcttaa attagagctt agatgactat agtattttaa tgttgtatta atgtcatcat    3120
gaccaagcct atcagctaca taaataatat ccatacccgc ttctacacat aagcctgtat    3180
gcgtatgtcg tagcttgtgt aatgtcactg gttcagaatt gattgtacta catatcttct    3240
tcaaagcttt attacaagac gcgttgtcta ctggcttatt gtggtaagtg atgaataata    3300
acatcaatgg attcttaata gcatgttcct tcatataatc agtatgccaa tttaaatacg    3360
aatgtaaata ttgagcggta gagttatcaa tatagatcac tcgtgatttt tttgttttgg    3420
tatcaatgaa tgtattagtg tacttgtaat cccaagcttt attcacagtt attgaacgtt    3480
tagtgaaatt aatatccttc tttgttagtg caataatttc ttcgaacctc atgcctgtct    3540
ggacagctag aaagataact gctcgtgata tagaatgaaa ttttgcaagt tcttctaata    3600
gtaaatgaac tttgtctgtt tccataaatt gtgctttatt tttcgctacg tcctgtccgc    3660
ttatatgagc ccctatagtg gggttttct tcatgtaacc taaatgaaca gccttgttaa    3720
aaatcgctct aattttgcgg tgtctggtgt ctacagtgga tattgcatag tctacagata    3780
aatgattaat aaattgttga tattgaaccg catcaatcga attaagttta attttttcat    3840
cgaaataatc aacgaattga ttataagcaa gatcgtataa attaatagta gattgactac    3900
ttttcccatc tttaaatgtt ttcatgaata gcgtataaaa ttctttgaag ttccattctt    3960
tcagagaact actatcatgc tgaacttgtt ttaataattt agatgcttta tacattaagt    4020
ttgtttcact tgtatctgtc aaacgctttt cttt ccatt c accatcgact tttatacgta    4080
ggcgaacaca atatttaccg tttgctaatt tttttatctt cattaatacc accacctgtt    4140 tattttttgga gatctttttt tcagaaaatc ccagtacgta attaagtatt tgagaattaa    4200
ttttatattg attaatacta agtttaccca gttttcacct aaaaaacaaa tgatgagata    4260
ataactccaa aggctaaaga ggactatacc aactatttgt aataattctg taacagttga    4320
aaagcgaacg tgtattctta gggcttgaga tgtactgctg ggtaaacctt tatagtgtaa    4380
gtgggatgtg aacgttaatc aacaactttc gctatgggaa acctattgtt ttttgttaat    4440
agaaaaactt aatacatttg taatataaaa accggcagtt tttccgttct tcgtgactcg    4500
aaatgaattg ccagatgagt ttatggtatt ctataataga aggtatggag gatgttatat    4560
aatgagacag aattatgatg atcgaaagct agcttggcac tggccgtcgt tttacaacgt    4620
cgtgactggg aaaaccctgg cgttacccaa cttaatcgcc ttgcagcaca tccccctttc    4680
gccagctggc gtaatagcga gaggcccgc accgatcgcc cttcccaaca gttgcgcagc    4740
ctgaatggcg aatggcgcct gatgcggtat tttctcctta cgcatctgtg cggtatttca    4800
caccgcatat caaatggttc ggatctggag ctgtaatata aaaaccttct tcaactaacg    4860
gggcaggtta gtgacattag aaaaccgact gtaaaagta cagtcggcat tatctcatat    4920
tataaaagcc agtcattagg cctatctgac aattcctgaa tagagttcat aaacaatcct    4980
gcatgataac catcacaaac agaatgatgt acctgtaaag atagcggtaa atatattgaa    5040
ttacctttat taatgaattt tcctgctgta ataatgggta gaaggtaatt actattatta    5100
ttgatattta agttaaaccc agtaaatgaa gtccatggaa taatagaaag agaaaaagca    5160
ttttcaggta taggtgtttt gggaaacaat ttccccgaac cattatattt ctctacatca    5220
gaaaggtata aatcataaaa ctctttgaag tcattcttta caggagtcca aataccagag    5280
aatgttttag atacaccatc aaaaattgta taaagtggct ctaacttatc ccaataacct    5340
aactctccgt cgctattgta accagttcta aaagctgtat ttgagtttat caccttgtc     5400
```

```
actaagaaaa taaatgcagg gtaaaattta tatccttctt gttttatgtt tcggtataaa      5460
acactaatat caatttctgt ggttatacta aaagtcgttt gttggttcaa ataatgatta      5520
aatatctctt ttctcttcca attgtctaaa tcaattttat taaagttcat ttgatatgcc      5580
tcctaaattt ttatctaaag tgaatttagg aggcttactt gtctgctttc ttcattagaa      5640
tcaatccttt tttaaaagtc aatattactg taacataaat atatatttta aaaatatccc      5700
actttatcca attttcgttt gttgaactaa tgggtgcttt agttgaagaa taaagaccac      5760
attaaaaaat gtggtctttt gtgttttttt aaaggatttg agcgtagcga aaaatccttt      5820
tctttcttat cttgataata agggtaacta ttgcccagat ccgaaccatt tgatatggtg      5880
cactctcagt acaatctgct ctgatgccgc atagttaagc cagccccgac acccgccaac      5940
acccgctgac gcgccctgac gggcttgtct gctcccggca tccgcttaca gacaagctgt      6000
gaccgtctcc gggagctgca tgtgtcagag gttttcaccg tcatcaccga aacgcgcgag      6060
acgaaagggc ctcgtgatac gcctattttt ataggttaat gtcatgataa taatggtttc      6120
tta                                                                   6123
```